United States Patent [19]
Muller et al.

[11] Patent Number: 5,633,227
[45] Date of Patent: May 27, 1997

[54] SECRETORY LEUKOCYTE PROTEASE INHIBITOR AS AN INHIBITOR OF TRYPTASE

[75] Inventors: Daniel K. Muller, Orange; Elise Brownell, Woodbridge; Katherine A. Delaria, West Haven, all of Conn.

[73] Assignee: Miles, Inc., West Haven, Conn.

[21] Appl. No.: 304,051

[22] Filed: Sep. 12, 1994

[51] Int. Cl.$^6$ .......... A61K 38/57; C07K 14/81; C12N 9/64

[52] U.S. Cl. .......... 514/12; 435/226; 530/324; 930/250

[58] Field of Search .......... 930/250; 530/300, 530/324, 350; 514/2, 12, 21, 826; 435/23, 226

[56] References Cited

U.S. PATENT DOCUMENTS

| | | | |
|---|---|---|---|
| 4,356,181 | 10/1982 | Payling et al. | 514/185 |
| 4,760,130 | 7/1988 | Thompson et al. | 530/350 |
| 4,845,076 | 7/1989 | Heinzel et al. | 514/12 |
| 4,845,242 | 7/1989 | Powers et al. | 549/283 |
| 4,916,117 | 4/1990 | Lezdey et al. | 514/8 |
| 5,089,634 | 2/1992 | Powers et al. | 549/285 |
| 5,166,134 | 11/1992 | Lezdey et al. | 514/21 |
| 5,190,917 | 3/1993 | Lezdey et al. | 514/12 |
| 5,215,965 | 6/1993 | Lezdey et al. | 514/21 |
| 5,217,951 | 6/1993 | Lezdey et al. | 514/8 |
| 5,290,762 | 3/1994 | Lezdey et al. | 514/8 |

FOREIGN PATENT DOCUMENTS

| | | | |
|---|---|---|---|
| 0346500A1 | 12/1989 | European Pat. Off. | C07K 3/08 |
| 0426860A1 | 5/1991 | European Pat. Off. | C12N 15/15 |
| 0503203A1 | 9/1992 | European Pat. Off. | C07K 5/08 |
| 0504064A1 | 9/1992 | European Pat. Off. | C07K 5/06 |
| WO86/03497 | 6/1986 | WIPO | C07K 7/10 |
| WO86/03519 | 6/1986 | WIPO | C12P 21/00 |

OTHER PUBLICATIONS

Agents and Actions, vol. 30, Nos. 1/2, issued 1990, Overveld, "Some aspects of mast cell subtypes from human lung tissue", pp. 24–29.

Biochemical Pharmacology, vol. 48, No. 4, issued 1994, Masuda et al, "Specific Cleavage of Secretory Leukoprotease Inhibitor . . . ", pp. 651–657.

Alter et al., "Interactions of Human Mast Cell Tryptase with Biological Protease Inhibitors", Arch. Biochem. Biophys. 276, 26–31 (1990).

Barnes, P. J., "Neuropeptides as Modulators of Airway Function", Mediators in Airway Hyperactivity, 175–196, (1990).

Caughey et al., "Substance P and Vasoactive Intestinal Peptide Degradation by Mast Cell Tryptase and Chymase", J. Pharmacol. Exp. Ther. 244, 133–137 (1988).

Crystal, R. G. and Roosdorp, N. J., "Aerosolization of Protein Therapeutic Agent", NTIS PAT–APPL–7 828 447 (1992).

Eisenberg et al., "Location of the Protease–inhibitory Region of Secretory Leukocyte Protease Inhibitor", J. Biol. Chem. 265, 7976–7981 (1990).

Grütter et al., "The 2.5 Å X–ray crystal structure of the acid–stable proteinase inhibitor from human mucous secretions analysed in its complex with bovine α–chymotrypsin", EMBO J. 7, 345–351 (1988).

Harvima et al., "Mast cell tryptase and chymase in developing and mature psoriatic lesions", Arch. Dermatol. Res. 285, 184–192 (1993).

(List continued on next page.)

*Primary Examiner*—Jeffrey E. Russel
*Attorney, Agent, or Firm*—William F. Gray

[57] ABSTRACT

This invention concerns methods of treating mast-cell mediated conditions in mammals, the methods comprising administering to the mammals pharmacologically active fragments or muteins of SLPI; methods of treating asthma or allergic rhinitis in mammals, the methods comprising administering to the mammals SLPI or pharmacologically active fragments or muteins thereof; methods for inhibiting tryptase; methods for identifying inhibitors of tryptase; and certain fragments and muteins of SLPI.

6 Claims, 9 Drawing Sheets

```
Met-Lys-Ser-Ser-Gly-Leu-Phe-Pro-Phe-Leu-
-25                                    -20
Val-Leu-Leu-Ala-Leu-Gly-Thr-Leu-Ala-Pro-
-15                                    -10
Trp-Ala-Val-Glu-Gly-Ser-Gly-Lys-Ser-Phe-
 -5              1                     5
Lys-Ala-Gly-Val-Cys-Pro-Pro-Lys-Lys-Ser-
                10                    15
Ala-Gln-Cys-Leu-Arg-Tyr-Lys-Lys-Pro-Glu-
                20                    25
Cys-Gln-Ser-Asp-Trp-Gln-Cys-Pro-Gly-Lys-
                30                    35
Lys-Arg-Cys-Cys-Pro-Asp-Thr-Cys-Gly-Ile-
                40                    45
Lys-Cys-Leu-Asp-Pro-Val-Asp-Thr-Pro-Asn-
                50                    55
Pro-Thr-Arg-Arg-Lys-Pro-Gly-Lys-Cys-Pro-
                60                    65
Val-Thr-Tyr-Gly-Gln-Cys-Leu-Met-Leu-Asn-
                70                    75
Pro-Pro-Asn-Phe-Cys-Glu-Met-Asp-Gly-Gln-
                80                    85
Cys-Lys-Arg-Asp-Leu-Lys-Cys-Cys-Met-Gly-
                90                    95
Met-Cys-Gly-Lys-Ser-Cys-Val-Ser-Pro-Val-
               100                   105
Lys-Ala
```

OTHER PUBLICATIONS

Heinzel et al., "Molecular cloning and expression of cDNA for human antileukoprotease from cervix uterus", Eur. J. Biochem. 160, 61–67 (1986).

Hochstrasser et al., "Interaction of human mast cell tryptase and chymase with low-molecular-mass serine proteinase inhibitors from the human respitory tract", Eur. Arch. Otorhinolaryngol. 249, 455–458 (1993).

Klasen, E. C. and Kramps, J. A. "The N-Terminal Sequence of Antileukoprotease Isolated from Bronchial Secretion", Biochem. Biophys. Res. Commun. 128, 285–289 (1985).

Kramps et al., "Proteinase inhibitory activities of antileukoprotease are represented by its second COOH-terminal domain", Biochim. Biophys. Acta. 1038, 178–185 (1990).

McElvaney et al., "Modulation of Airway Inflammation in Cystic Fibrosis", J. Clin. Invest. 90, 1296–1301 (1992).

Meckelein et al., "The location on inhibitory specificities in human mucus proteinase inhibitor (MPI): separate expression of the COOH-terminal domain yeilds an active inhibitor of three different proteinases", Protein Eng. 3, 215–220 (1990).

Ollerenshaw et al., "Absence of Immunoreactive Vasoactive Intestinal Polypeptide in Tissue from the Lungs of Patients with Asthma", N. Engl. J. Med. 320, 1244–1248 (1989).

Renesto et al., "Inhibition by recombinant SLPI and half-SLPI ($Asn^{55}$–$Ala^{107}$) of elastase and cathepsin G activities: consequence for neutrophil–platelet cooperation", Br. J. Pharmacol. 108, 1100–1106 (1993).

Schwartz, L. B. and Bradford, T. R., "Regulation of Tryptase from Human Lung Mast Cells by Heparin", J. Biol. Chem. 261, 7372–7379 (1986).

Seemüller et al., "The acid-stable proteinase inhibitor of human mucous secretions (HUSI-I, antileukoprotease)", FEBS Lett. 199, 43–48 (1986).

Smith et al., "Human Lung Tryptase", J. Biol. Chem. 259, 11046–11051 (1984).

Stolk et al., "Potency of an Oxidation-resistant Mutant of Secretory Leukocyte Proteinase Inhibitor in Lipopolysaccharide-induced Emphysema in Hamsters", Pul. Pharmacol. 6, 33–39 (1993).

Tam, E. K. and Caughey, G. H., "Degradation of Airway Neuropeptides by Human Lung Tryptase", Am. J. Respir. Cell. Mol. Biol. 3, 27–31 (1990).

Tanaka et al., "Mast Cell Tryptase, A New Target For Therapeutic Intervention In Asthma", Poster session handout for Symposium on Immunoregulation of Asthma II, Jun. 23, 1994, Quebec, Canada.

Thompson, R. C. and Ohlsson K., "Isolation, properties, and complete amino acid sequence of human secretory leukocyte protease inhibitor, a potent inhibitor of leukocyte elastase", Proc. Natl. Acad. Sci. USA 83, 6692–6696 (1986).

Van-Seuningen, I. and Davril, M., "Separation of the two domains of human mucus proteinase inhibitor : inhibitory activity is only located in the carboxy-terminal domain", Biochem. Biophys. Res. Commun. 179, 1587–1592 (1991).

Vogelmeier et al., "Aerolization of recombinant SLPI to augment antineutrophil elastase protection of pulmonary epithelium" 69, 1843–1848 (1990).

Wenzel et al., "Activation of Pulmonary Mast Cells by Bronchoalveolar Allergen Challenge", 137, 1002–1008 (1988).

Ying et al., "Functions of the N-Terminal Domain of Secretory Leukoprotease Inhibitor", Biochemistry 33, 5445–5450 (1994).

VIP Assay

GPK-AMC assay

```
Met-Lys-Ser-Ser-Gly-Leu-Phe-Pro-Phe-Leu-
-25                      -20
Val-Leu-Leu-Ala-Leu-Gly-Thr-Leu-Ala-Pro-
-15                      -10
Trp-Ala-Val-Glu-Gly-Ser-Gly-Lys-Ser-Phe-
 -5                       1                    5
Lys-Ala-Gly-Val-Cys-Pro-Pro-Lys-Lys-Ser-
                         10                   15
Ala-Gln-Cys-Leu-Arg-Tyr-Lys-Lys-Pro-Glu-
                         20                   25
Cys-Gln-Ser-Asp-Trp-Gln-Cys-Pro-Gly-Lys-
                         30                   35
Lys-Arg-Cys-Cys-Pro-Asp-Thr-Cys-Gly-Ile-
                         40                   45
Lys-Cys-Leu-Asp-Pro-Val-Asp-Thr-Pro-Asn-
                         50                   55
Pro-Thr-Arg-Arg-Lys-Pro-Gly-Lys-Cys-Pro-
                         60                   65
Val-Thr-Tyr-Gly-Gln-Cys-Leu-Met-Leu-Asn-
                         70                   75
Pro-Pro-Asn-Phe-Cys-Glu-Met-Asp-Gly-Gln-
                         80                   85
Cys-Lys-Arg-Asp-Leu-Lys-Cys-Cys-Met-Gly-
                         90                   95
Met-Cys-Gly-Lys-Ser-Cys-Val-Ser-Pro-Val-
                        100                  105

Lys-Ala
```

Fig. 9

SECRETORY LEUKOCYTE PROTEASE INHIBITOR AS AN INHIBITOR OF TRYPTASE

FIELD

This invention relates to inhibition of proteases, and more particularly, to inhibition of tryptase by secretory leukocyte protease inhibitor (SLPI).

BACKGROUND

Vasoactive intestinal peptide (VIP) is a bronchorelaxant which is absent from or present only at relatively low levels in the lungs of asthmatics, but present in lungs of nonasthmatics. See Ollerenshaw et al., N. Engl. J. Med., 320, 1244–1248 (1989). This implies that VIP is a factor in normal lung function and that its depletion may play a causal role in the pathogenesis of asthma. VIP is degraded by tryptase, a serine protease which is found in large quantities in mast cells and is released upon mast cell degranulation. See Tam and Caughey, Am. J. Respir. Cell Mol. Biol., 3, 27–32 (1990); and Wenzel et al., Am. Rev. Respir. Dis., 137, 1002–1008 (1988). Thus, it has been hypothesized that if tryptase action in the lung could be inhibited, VIP levels would be higher than if the action of tryptase were not inhibited. Tryptase inhibition logically provides a method of treatment for mast-cell mediated diseases, e.g., asthma.

The activities of extracellular proteases are usually tightly controlled through the secretion of protein-based inhibitors. See Travis et al., Ann. Rev. Biochem., 52, 655–709 (1983). No biological inhibitors for tryptase have been disclosed in the literature to date. Many known serine protease inhibitors, including secretory leukocyte protease inhibitor (SLPI, also known as human seminal inhibitor-I (HUSI-I) and antileukoprotease-1 (ALP-1)) have been tested as tryptase inhibitors. See Smith et al., J. Biol. Chem., 259, 11046–11051 (1984); Hochstrasser et al., Eur. Arch. Otorhinolaryngol., 249, 455–458 (1993); and Alter et al., Arch. Biochem. and Biophys., 276, 26–31 (1990). Little or no tryptase inhibitory activity has been reported, however.

It would be desirable to have tryptase inhibitors, a procedure for identifying such inhibitors, and means for treating mast cell- and/or tryptase-related disorders. Such advances in the art are the subject of the present invention.

SUMMARY

The applicants have now discovered that SLPI is a potent inhibitor of the proteolytic activity of tryptase. SLPI inhibits tryptase degradation of VIP with a $K_i$ value of approximately 8 nM, indicating that there is a tight, pharmacologically useful interaction between SLPI and tryptase. This is the first identification of a naturally-occurring human protein that can inhibit tryptase.

Given the tight interaction demonstrated between SLPI and tryptase, it is possible to reach pharmacologically useful levels of SLPI in the body, e.g., for the treatment of asthma and other mast cell mediated diseases, as well as diseases in which the levels of tryptase activity are elevated due to increased protein production, decreased clearance, or decreased inhibitor levels.

The discovery of the ability of SLPI to inhibit tryptase was facilitated by the applicants' development of an improved assay to measure the proteolytic activity of tryptase on a biologically relevant substrate, e.g., vasoactive intestinal peptide (VIP). This peptide was provided with a suitable reporter group such as dansyl on its N-terminus, then used as a substrate for tryptase in the assay. The degradation products were separated, and the concentration of the VIP or labelled fragments was determined from the fluorescence of the dansyl group.

In one of its aspects, the invention relates to a method for treating a mast cell-mediated condition in a mammal, which comprises administering to such mammal an amount of a pharmacologically active fragment of SLPI or mutein thereof which is effective to treat the mast cell-mediated condition.

In another of its aspects, the invention relates to a method for treating the conditions of asthma and allergic rhinitis in a mammal, which comprises administering to such mammal an amount of SLPI or a pharmacologically active fragment or mutein thereof which is effective to treat the condition.

In yet another of its aspects, the invention relates to a method of inhibiting tryptase, which comprises contacting tryptase with an amount of SLPI or a pharmacologically active fragment or mutein thereof which is effective to inhibit the proteolytic activity of the tryptase.

In a further aspect, the invention relates to a method for identifying inhibitors of tryptase activity, comprising the following steps:

(a) providing tryptase or tryptase-containing material having an assayable amount of enzymatic activity;

(b) incubating the tryptase or tryptase-containing material with a test substance to be assayed for its ability to inhibit tryptase activity;

(c) adding a tryptase substrate which is a synthetic peptide comprising at least 10 amino acids and a detectable label;

(d) monitoring cleavage of the tryptase substrate as a function of time; and (e) determining the inhibitory effect of the test substance on tryptase by comparing the cleavage of the substrate by tryptase in the absence and presence of test substance.

BRIEF DESCRIPTION OF THE DRAWINGS

The invention will be better understood from a consideration of the following detailed description (see following glossary for abbreviations used), taken in conjunction with the drawing, in which.

Figure 6A:
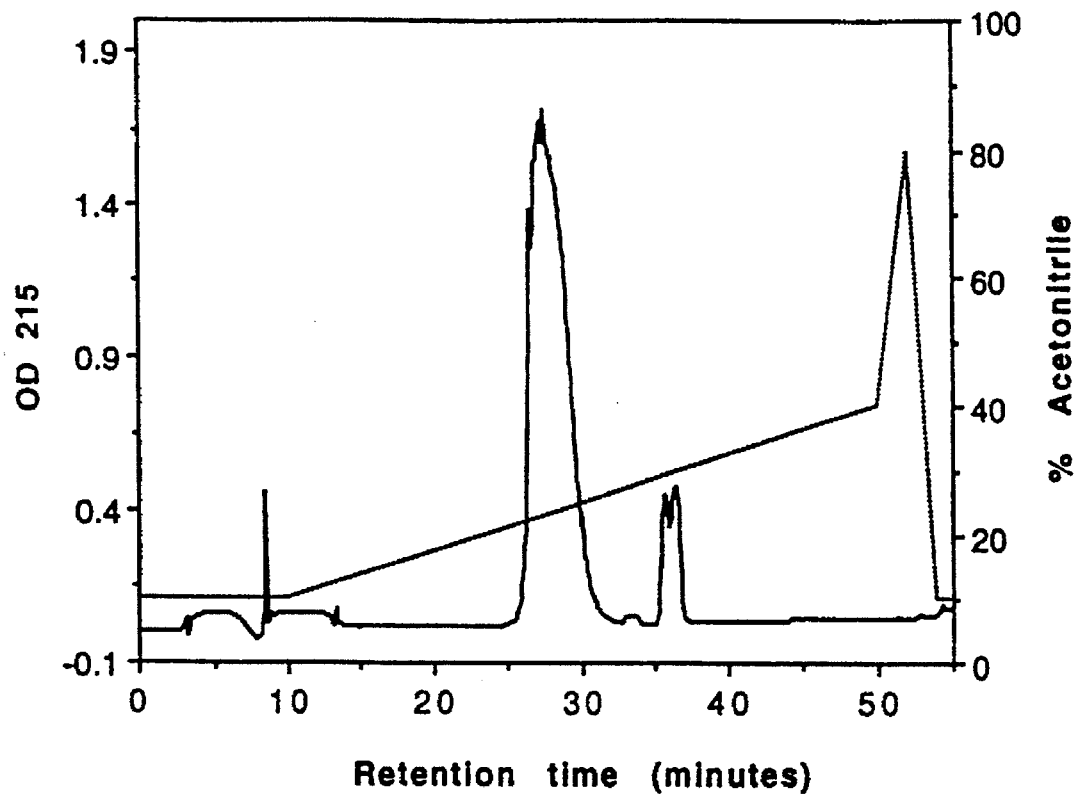
Figure 6B:
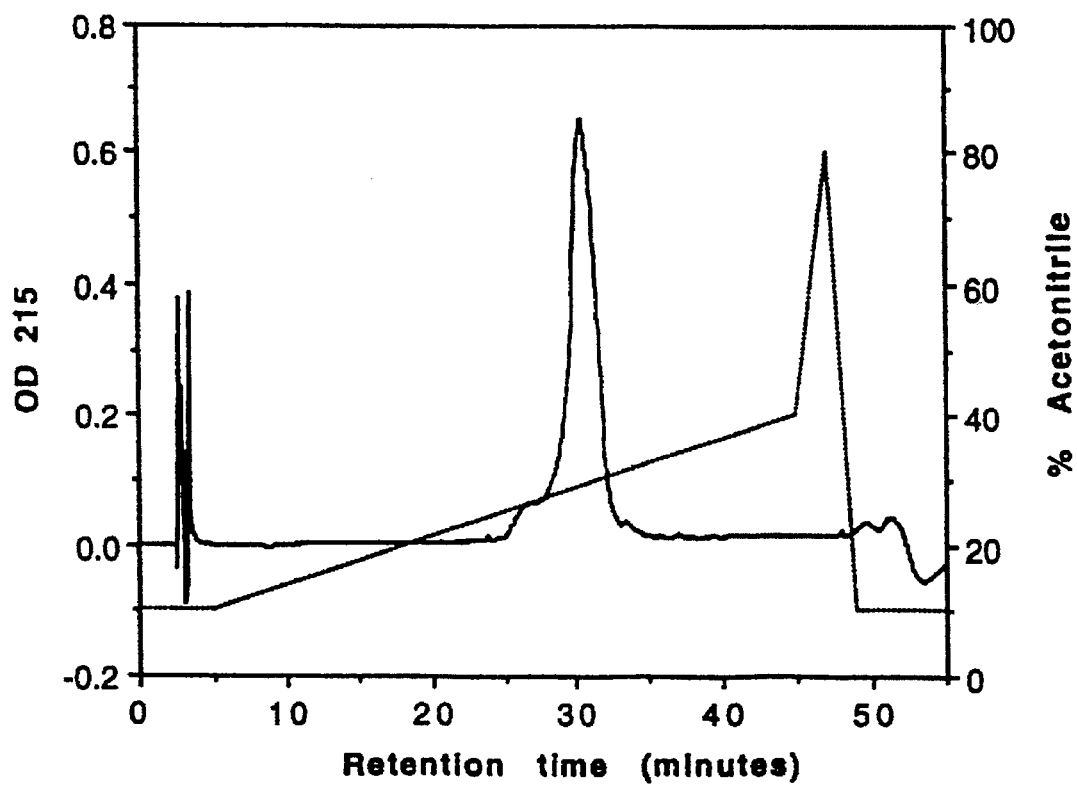
Figure 7A:
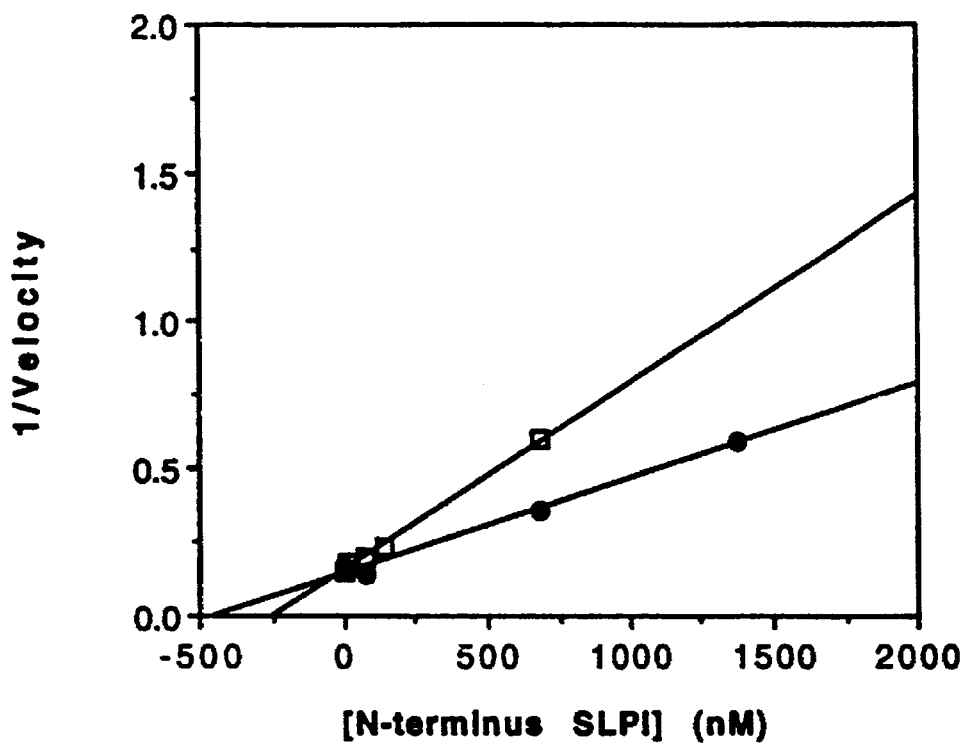
Figure 7B:
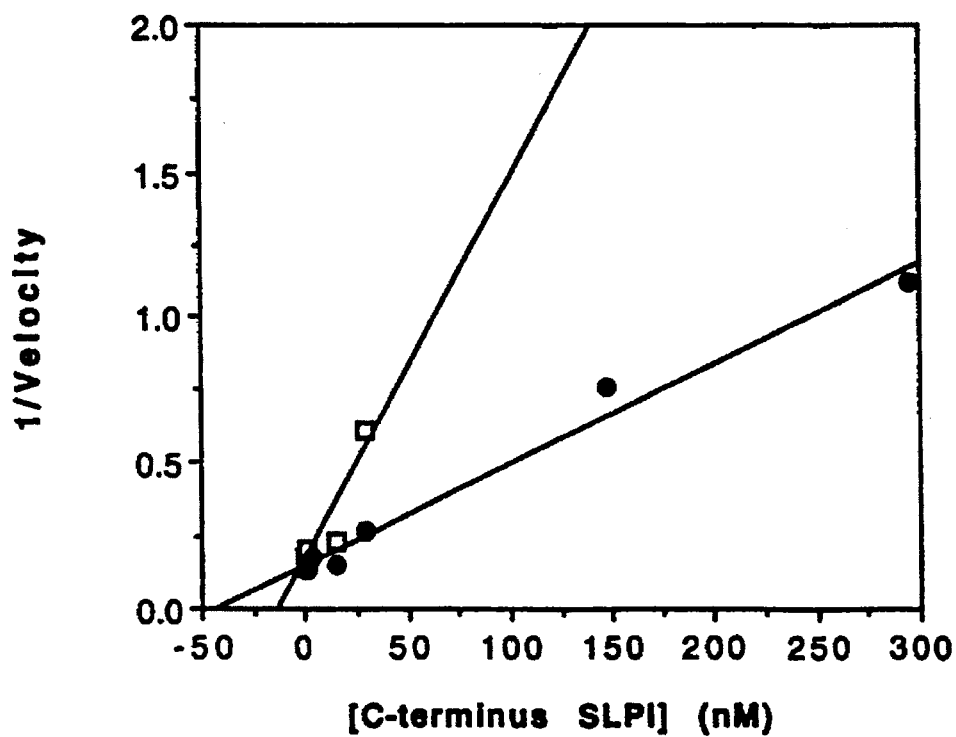
Figure 8A:
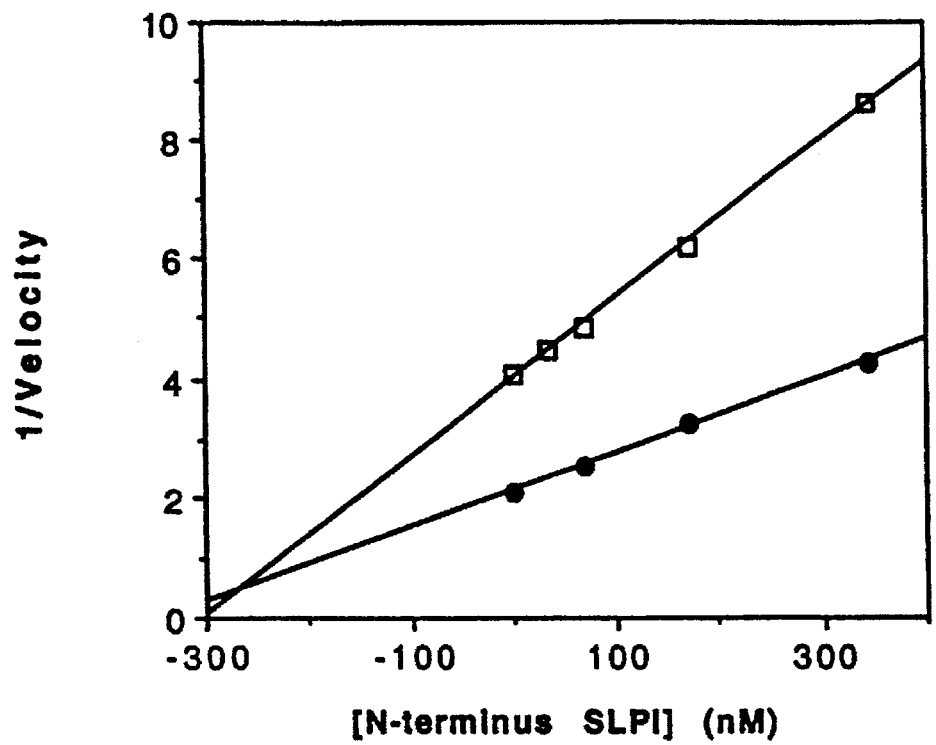
Figure 8B:
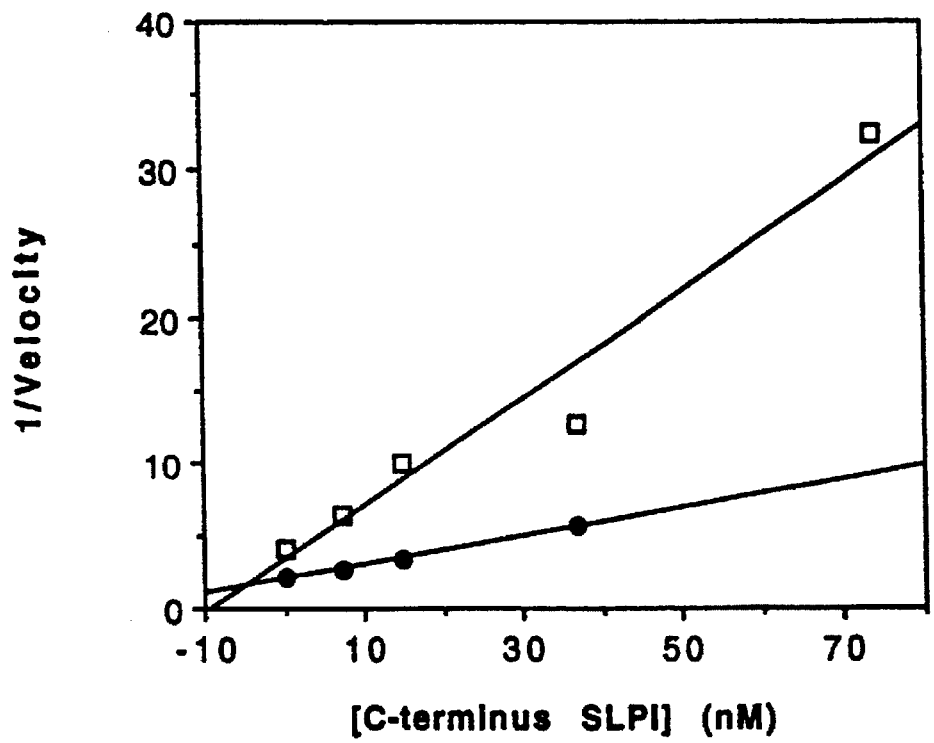

FIGS. 6A and 6B show the HPLC elution profiles of the N- and C-terminal domains, respectively, of acid-treated SLPI from a C-18 column; 6A shows absorbance at 215 nm (solid line) and elution gradient (dashed line) vs. retention time for peak 1 from the C-8 column; 6B shows the same analysis as in FIG. 6A but for peak 2 from the C-8 column;

FIGS. 7A and 7B show Dixon plots for the inhibition of the proteolytic activity of tryptase by the N- and C-terminal domains of SLPI, respectively, in the VIP assay at 0.4 (squares) and 0.8 (circles) μM VIP, the rate of formation of the Dns-VIP-(1-14) degradation product being monitored;

FIGS. 8A and 8B show Dixon plots for the inhibition of the proteolytic activity of tryptase by the N- and C-terminal domains of SLPI, respectively, in the GPK assay at 20 (squares) and 40 (circles) μM GPK-AMC;

FIG. 9 shows the amino acid sequence of SLPI.

DETAILED DESCRIPTION

This invention is based on the discovery that SLPI inhibits tryptase, a serine protease which is a major protein constituent of mast cells. In addition, a number of fragments which retain tryptase-inhibiting properties have been identified. Accordingly, mast cell- or tryptase-mediated conditions may be treated by administering SLPI or pharmacologically active fragments or muteins thereof.

The conditions which may be treated by the method of the invention include, e.g., asthma and allergic rhinitis.

Both the SLPI and the active SLPI fragments which are useful in the invention may be of natural, synthetic, or recombinant origin. Full-length SLPI may be purchased commercially; alternatively, SLPI may be isolated from natural sources such as seminal plasma, cervical secretions, and bronchial secretions by methods well-known to those skilled in the art, see, e.g. Thompson et al., Proc. Natl. Acad. Sci. USA, 83, 6692–6696 (1986); Klasen and Kramps, Biochem. Biophys. Res. Commun., 128, 285–289 (1985). The DNA sequence of full-length SLPI is known, see, e.g., Heinzel et al., Eur. J. Biochem., 160, 61–67 (1987) and accordingly, SLPI can be cloned according to methods well-known to those skilled in the art; see, e.g., Heinzel, above.

The SLPI fragments may be the SLPI N-terminal domain of amino acids 1-49, the C-terminal domain of amino acids 50-107, smaller but still active portions of these fragments, or SLPI fragments which encompass some part of both the N- and C-terminal domains of SLPI, and muteins thereof.

Examples of particular peptides which may be used are the amino acid sequences 57-107, 57-102, and 5-49 of human SLPI (see FIG. 9), the Leu-72-Arg and Leu-72-Lys muteins of the 57-107 and 57-102 sequences of human SLPI, the Leu-19-Arg and Leu-19-Lys muteins of the 5-49 sequence of human SLPI, and muteins of a fragment of human SLPI having the amino acid sequence: Ser-Gly-Lys-Ser-Phe-Lys-Ala-Gly-Val-Cys-Pro-Lys-Lys- Ser-Ala-Gln-Cys-Xaa-Leu-Arg-Tyr-Lys-Lys-Pro-Glu-Cys-Gln-Ser-Asp-Trp-Gln-Cys-Pro-Gly-Lys-Lys-Arg-Cys-Cys-Pro-Asp-Thr-Cys-Gly- Ile-Lys-Cys-Leu-Asp wherein Xaa is Arg or Lys [SEQ ID NO: 1]. Examples of useful peptides containing portions of both the N-and C-terminal domains are the 5-102 amino acid sequence of human SLPI and muteins thereof.

Preparation of the N- and C-terminal domains of the SLPI molecule is accomplished by hydrolyzing full-length SLPI under mild acid conditions, as exemplified below. Other fragments of the SLPI molecule may be prepared as disclosed in the following text.

Fragments of the SLPI protein can be synthesized or produced either in bacteria, from the pET-3d vector, or in baculovirus vectors such as pVL1392 or pAc-GP67. DNA fragments coding for the 57-107 and 57-102 sequences of the C-terminal domain of SLPI can be produced using the polymerase chain reaction using primers 4/5 and 4/7, respectively, in Table I. The Leu-72-Arg mutation of 57-107 can be made using primers 5/6 and the Leu-72-Lys version can be prepared with primers 5/10. The Leu-72-Arg mutation of 57-102 can be prepared using primers 6/7 and the Leu-72-Lys version can be prepared with primers 7/10.

TABLE I

Primers for SLPI Amplification

| # Sequence |
|---|
| 1. GTC GCG GCC GCC TTC ACC ATG AAG TCC AGC [SEQ ID NO: 2] |
| 2. GGG GAA TTC TGG CAG GAA TCA AGC TTT CAC AGG [SEQ ID NO: 3] |
| 3. GGG GAA TTC TCA GTT TGG GGT GTC AAC AGG [SEQ ID NO: 4] |
| 4. GGG CCA TGG CAA CAA GA GGA AGC CTG GGA AG [SEQ ID NO: 5] |
| 5. CCC GGA TCC GAA TCA AGC TTT CAC AGG GGA AAC [SEQ ID NO: 6] |
| 6. GGG CCA TGG CAA CAA GGA GGA AGC CTG GGA AGT GCC CAG TGA CTT ATG GCC AAT GTA GGA TGC TTA ACC CCC CCA ATT TC [SEQ ID NO: 7] |
| 7. CCC GGA TCC TCA AAC GCA GGA TTT CCC ACA CAT G [SEQ ID NO: 8] |
| 8. GGG CCA TGG CCT TCA AAG CTG GAG TCT GTC C [SEQ ID NO: 9] |
| 9. GGG AGA TCT CAA TCC AGG CAT TTG ATG CCA CAA GTG TC [SEQ ID NO: 10] |
| 10. GGG CCA TGG CAA CAA GGA GGA AGC CTG GGA AGT GCC CAG TGA CTT ATG GCC AAT GTA AGA TGC TTA ACC CCC CCA ATT TC [SEQ ID NO: 11] |
| 11. GGG CCA TGG GCT CTG GAA AGT CCT TCA AAG CTG GAG TCT GTC CTA AGA AAT CTG CCC AGT GCA GAC TTA GAT ACA AGA AAC CTG AGT GC [SEQ ID NO: 12] |
| 12. GGG CCA TGG GCT CTG GAA AGT CCT TCA AAG CTG GAG TCT GTC |

TABLE I-continued

Primers for SLPI Amplification

| # | Sequence |
|---|---|
| | CTA AGA AAT CTG CCC AGT GCA AGC TTA GAT ACA AGA AAC CTG AGT GC [SEQ ID NO: 13] |
| 13. | GGG GGG GAA TTC TCA AAC GCA GGA TTT CCC ACA CAT G [SEQ ID NO: 14] |
| 14. | GGG GGG CCA TGG GCT CTG GAA AGT CCT TCA AAG CTG GAG TCT GTC CTC CTA AGA AAT CTG CCC AGT GCA GAA GAT ACA AGA AAC CTG AGT GCC [SEQ ID NO: 15] |
| 15. | GGG GGG CCA TGG GCT CTG GAA AGT CCT TCA AAG CTG GAG TCT GTC CTC CTA AGA AAT CTG CCC AGT GCA AGA GAT ACA AGA AAC CTG AGT GCC [SEQ ID NO: 16] |

[Engineered restriction sites are indicated in bold face type.]

The resulting DNA fragments are cloned into the appropriate expression vector using the restriction sites listed in Table II:

TABLE II

| Construct (residues of wild-type SLPI) | Primers Used | Restriction Sites |
|---|---|---|
| Full length SLPI (−25 to 107) | 1/2; PCR of human lung RNA | NotI/EcoRI into pUC 21 (not expressed) |
| N-terminal (−25 to 55) | 1/3: PCR using full length as template | NotI/EcoRI into pUC 21; NotI/PvuII into NotI/SmaI of Baculovirus pVL 1392 |
| C-terminal wild type (57 to 107) | 4/5; PCR using full length as template | NcoI/BamHI into pEt 3d; NcoI/BamHI into pAc GP67 cut with NcoI/BglII |
| C-terminal, Leu-72-Arg (57 to 107) | 5/6; PCR using full length as template | NcoI/BamHI into pET 3d; NcoI/BamHI into pAc GP67 cut with NcoI/BglII |
| Short C-terminal, wild type (57 to 102) | 4/7; PCR using full length as template | NcoI/BamHI into pAc GP67 cut with NcoI/BglII; NcoI/BamHI into pET 3d |
| Short C-terminal, Leu-72-Arg (57 to 102) | 6/7; PCR using full lenth as template | NcoI/BamHI into pAc GP67 cut with NcoI/BglII; NcoI/BamHI into pET 3d |
| Short N-terminal, (5 to 49) | 8/9: PCR using full length as template | NcoI/BglII into NcoI/BglII of pAc GP67 |
| Short N- + C-terminals, (5 to 102) | 13/8: PCR using full lenth as template | NcoI/EcoRI into pAc GP67 cut with NcoI/EcoRI |
| C-terminal, Leu-72-Arg (57 to 107) | 5/10: PCR using full length as template | NcoI/BamHI into pET 3d; pAc GP67 cut with NcoI/BglII |
| Short C-terminal, Leu-72-Arg (57 to 102) | 7/10: PCR using full length as template | NcoI/BamHI into pET 3d; pAc GP67 cut with NcoI/BglII |
| N-terminal mutein (5 to 49) desPro-11, Arg inserted between 18–19 | 9/11: PCR using full length as template | NcoI/BglII into NcoI/BglII of pAc GP67 |
| N-terminal mutein (5 to 49) desPro-11, Lys inserted between 18–19 | 9/12: PCR using full length as template | NcoI/BglII into NcoI/BglII of pAc GP67 |
| N-terminal Leu-19-Arg (5 to 49) | 9/14: PCR using full length as template | NcoI/BglII into NcoI/BglII of pAc GP67 |
| N-terminal Leu-19-Lys (5 to 49) | 9/15: PCR using full length as template | NcoI/BglII into NcoI/VglII of pAc GP67 |

The genes are then expressed in bacteria with an extra methionine and an extra alanine residue at the N-terminus to allow for the initiation of translation. In addition, these SLPI fragments can be expressed in the baculovirus system with a naturally-occurring baculovirus leader sequence to allow for proper processing and excretion of the expressed protein in an active state. However, the baculovirus-expressed material contains seven additional amino acids derived from the leader sequence. The Leu-72-Arg and Leu-72-Lys mutations should result in a substantial decrease in the $K_i$ value for the inhibition of tryptase compared to the wild type SLPI sequence.

In addition, DNA fragments coding for the 5-49 sequence of the N-terminal domain of SLPI can be produced using the polymerase chain reaction and primers 8/9. These fragments can be expressed in the baculovirus system using the native SLPI leader sequence to allow for proper processing and excretion of the active protein. Further, the Leu-19-Arg and Leu-19-Lys mutations can be made within the 5-49 sequence using primers 9/14 and 9/15, respectively. Two novel sequences derived from the N-terminus of SLPI can be constructed using primers 9/11 and 9/12 producing [SEQ ID No:1]. A fragment of SLPI, 5-102 containing parts of both the N- and C-terminal domains of SLPI can be produced by the polymerase chain reaction using primers 8/13.

Further experimental details of the preparations are known to the skilled in the art and require no further elaboration here.

The method of treating mast cell- or tryptase-mediated conditions may be practiced in mammals which exhibit such conditions.

The inhibitors of the present invention are contemplated for use in veterinary and human applications. For such purposes, they will be employed in pharmaceutical compositions containing active ingredient(s) plus one or more pharmaceutically acceptable carriers, diluents, fillers, binders, and other excipients, depending on the administration mode and dosage form contemplated.

Administration of the SLPI or pharmacologically active fragments or muteins thereof may be by any suitable mode known to those skilled in the art. Examples of suitable parenteral administration include intravenous, subcutaneous and intramuscular routes. Intravenous administration can be used to obtain acute regulation of peak plasma concentrations of the drug as might be needed for example to treat acute episodes of airway hyperresponsiveness. Improved half-life and targeting of the drug to the airway epithelia may be aided by entrapment of the drug in liposomes. It may be possible to improve the selectivity of liposomal targeting to the airways by incorporation of ligands into the outside of the liposomes that bind to airway-specific macromolecules. Alternatively intramuscular or subcutaneous depot injection with or without encapsulation of the drug into degradable microspheres e.g comprising poly(DL-lactide-co-glycolide) may be used to obtain prolonged sustained drug release as may be necessary to suppress the development of airway hyperresponsiveness. For improved convenience of the dosage form it may be possible to use an i.p. implanted reservoir and septum such as the Percuseal system available from Pharmacia. Improved convenience and patient compliance may also be achieved by the use of either injector pens (e.g. the Novo Pin or Q-pen) or needle-free jet injectors (e.g. from Bioject, Mediject or Becton Dickinson). Prolonged zero-order or other precisely controlled release such as pulsatile release can also be achieved as needed using implantable pumps. Examples include the subcutaneously implanted osmotic pumps available from ALZA, such as the ALZET osmotic pump.

Nasal delivery may be achieved by incorporation of the protein drug into bioadhesive particulate carriers (<200 µm) such as those comprising cellulose, polyacrylate or polycarbophil, in conjunction with suitable absorption enhancers such as phospholipids or acylcarnitines. Available systems include those developed by DanBiosys and Scios Nova.

Oral delivery may be achieved by incorporation of the drug into enteric coated capsules designed to release the drug into the colon where digestive protease activity is low. Examples include the OROS-CT/Osmet™ and PULSIN-CAP™ systems from ALZA and Scherer Drug Delivery Systems respectively. Other systems use azo-crosslinked polymers that are degraded by colon specific bacterial azoreductases, or pH sensitive polyacrylate polymers that are activated by the rise in pH at the colon. The above systems may be used in conjunction with a wide range of available absorption enhancers.

Targeted delivery of high doses of the drug to the site of airway hyperresponsiveness can be most directly achieved by pulmonary delivery. The lower airway epithelia are highly permeable to wide range of proteins of molecular sizes up to 20 kDa (e.g granulocyte colony stimulating factor). It is possible to spray dry proteins in suitable carriers such as mannitol, sucrose or lactose. Micron-sized particles may be delivered to the distal alveolar surface using dry powder inhalers similar in principle to those designed by Inhale, Dura, Fisons (Spinhaler), Glaxo (Rotahaler) or Astra (Turbohaler) propellant-based metered dose inhalers. Solution formulations with or without liposomes may be delivered using ultrasonic nebulizers. See the following references for further discussion of this topic: McElvaney, et al., J. Clin. Invest., 90, 1296–1301 (1992); and Vogelmeier et al., J. Appl. Physiol., 69, 1843–1848 (1990).

The amount of the pharmaceutical composition to be employed will depend on the recipient and the condition being treated. The requisite amount may be determined without undue experimentation by protocols known to those skilled in the art. Alternatively, the requisite amount may be calculated, based on a determination of the amount of tryptase which must be inhibited in order to treat the condition. As the active materials contemplated in this invention are deemed to be nontoxic, treatment preferably involves administration of an excess of the optimally required amount of active agent.

Regarding the process of inhibiting tryptase by contacting it with SLPI, the discussion above relating to possible sources of the SLPI and active SLPI fragments, the conditions which may be treated, possible SLPI fragments and muteins, and preparation of the active fragments also applies. In addition, however, this aspect of the invention applies not only to mammals, but also has other applications, including purification of tryptase and analysis of biological tissues for tryptase.

To facilitate further study of the physical and biological properties of tryptase, it is desirable to have highly purified enzyme, substantially free of contaminants. In the prior art, tryptase is purified from a homogenate of human lung using a series of chromatographic steps. This purification procedure is complex, time consuming, provides poor yields, and can result in tryptase which is not completely homogeneous. Further, to determine the role of tryptase in the development of disease, it is necessary to be able to determine conveniently the concentration of tryptase in various biological samples.

The present invention answers these needs by providing 1) an improved method for purifying tryptase, and 2) an improved method for determining tryptase in biological fluids and extracts. Both of these improved procedures are based on applicants' discovery that SLPI is an inhibitor of tryptase. The method of purification is simpler, more convenient, faster, and results in higher yields and more highly purified enzyme than the prior art purification procedure. The procedure for determining tryptase allows the concentration of active tryptase in a sample to be determined, as opposed to a determination of total tryptase, some of which may be inactive or complexed with an inhibitor.

Regarding the claimed method for identifying inhibitors of tryptase activity, the following comments may be made.

The tryptase or tryptase-containing material having an assayable amount of enzymatic activity is purified or commercially-obtained tryptase, or tryptase-containing tissue such as lung or skin. Preparation of tissue samples involves extraction as discussed below.

The test substance to be assayed for its ability to modulate tryptase activity is a natural or synthetic compound. Examples include commercially available proteins, conditioned media from cell lines, and various tissue extracts.

The tryptase substrate is a labeled peptide or protein. Examples of naturally occurring tryptase substrates are the VIP employed in this application, CGRP, PHM, and muteins thereof. Examples of suitable labels are the dansyl, dabcyl, Abz, and fluorsceinyl groups.

Detection of the unreacted labeled substrate or the cleavage product of the reaction between tryptase and the labeled substrate is a function of the particular label used. In the case of the above-listed labels, the reaction mixtures are separated by HPLC, and the fluorescence of the labeled materials is monitored at an appropriate wavelength.

Finally, the inhibitory effect of a range of test substance concentrations is determined by measuring the reaction rates at a minimum of two different substrate concentrations, and constructing a Dixon plot (1/velocity vs inhibitor concentration), from which the type of inhibitor and the $K_i$ value are obtained.

Experimental

Further understanding of the invention may be derived from a consideration of the following examples.

Glossary of Materials, Terms, Sources, etc.

Abz stands for the group 2-aminobenzoyl(anthranilyl).

Acetonitrile (HPLC grade) was purchased from J. T. Baker (Philadelphia, Pa.).

ACN stands for acetonitrile.

Abz-His-Lys-Ala-Arg-Val-Leu-Xaa-Glu-Ala-Nle-Ser-NH$_2$ [SEQ ID NO: 20], wherein Xaa is p-nitro-Phe, was obtained from BACHEM Bioscience (Cat. No. H-1044).

Anhydrotrypsin-Sepharose was obtained from Takara Biochemical, Inc., Berkeley, Calif.

Anti-tryptase monoclonal antibody was obtained from Dako (U.K.).

Baculovirus vector pVL 1392 is available from Invitrogen, San Diego, Calif; pAc GP67 is available from Pharmingen, San Diego, Calif.

BOC stands for the t-butyloxycarbonyl group.

CGRP stands for calcitonin gene-related peptide.

Cyanogen bromide-activated sepharose is obtained from Pharmacia, Piscataway, N.J.

Dabcyl stands for the 4-(4-dimethylamino phenylazo)-benzoyl group.

Dansyl histidine was purchased from Research Plus (Bayonne, N.J.).

DMSO stands for dimethylsulfoxide, available from the Aldrich Chemical Co. (Milwaukee, Wis.).

E-64 is N-[N-(L-3-trans-carboxyoxiran-2-carbonyl)-L-leucyl-agmatine and is available from Sigma Chemical Co. (St. Louis, Mo.).

Ethanedithiol was purchased from the Aldrich Chemical Co. (Milwaukee, Wis.).

GPK-AMC stands for Gly-Pro-Lys-Aminomethylcoumarin.

Heparin (procine mucosal) was obtained from Sigma Chemical Co., St. Louis, Mo.

Heparin-sepharose was obtained from Pharmacia (Piscataway, N.J.).

High salt buffer is 10 mM MES at pH 6.1, 2.0M NaCl, and 0.02 % sodium azide.

Low salt buffer is 20 mM MES at pH 6.1, 150 mM NaCl, and 0.02 % sodium azide.

MES is 2-(N-morpholino)ethanesulfonic acid and is obtained from Sigma Chemical Co. (St. Louis, Mo.).

Micro-vials for the auto-injector on the HP1090 were obtained from SunBrokers (Wilmington, N.C.).

MWCO stands for "molecular weight cut off".

NMP-HBTU Fmoc chemistry is chemistry based on N-methylpyrrolidone/2-(1H-benzotriazole-1-yl)-1,1,3,3-tetramethyl-uronium hexafluorophosphate/9-fluorenylmethoxy-carbonyl Octyl-sepharose was obtained from Pharmacia (Piscataway, N.J.).

pET 3d vector is available from Novagen, Madison, Wis. by license.

PHM stands for peptide histidine-methionine and is available from Sigma Chemical Co. (St. Louis, Mo.).

PMC stands for the 2,2,5,7,8-pentamethylchroman-6-sulfonyl group.

PTC amino acid analysis (where PTC stands for phenylthiocarbamoyl) was carried out in accordance with the procedure of Dupont, D. R., Keim, P. S., Chui, A. H., Bello, R., Bozzini, M., and Wilson, K. J. in *Techniques in Protein Chemistry: A comprehensive approach to amino acid analysis* (Hugli, T. E., Ed) pp. 284–294, Academic Press, San Diego, (1989).

pVL 1392 is a baculovirus vector available from Invitrogen, San Diego, Calif.

Rink resin was obtained from Novabiochem (La Jolla, Calif.).

Sample buffer (1X) is 0.45M Tris (pH 8.5), 2.25% SDS, 10% glycerol plus 2.5% BME, where SDS stands for sodium dodecyl sulfate, and BME stands for beta-mercaptoethanol.

SDS-PAGE tricine buffered gels were obtained from Novex, San Diego, Calif. SDS-PAGE stands for sodium dodecyl sulfate-polyacrylamide gel electrophoresis and tricine stands for N-[tris-(hydroxymethyl)-methyl]glycine.

SLPI stands for secretory leukocyte protease inhibitor. This material is also known by other names, including the following: bronchial inhibitor, human seminal inhibitor-1 (HUSI-1), antileucoprotease-1 (ALP-1), cervix-uterus-secretion inhibitor (CUSI-1), and bronchial-secretion inhibitor (BSI). Recombinant SLPI was purchased from R+D Systems (Minneapolis, Minn.).

Sodium acetate was purchased from the Sigma Chemical Co. (St. Louis, Mo.).

System Gold software was used with the Beckman model 126 HPLC and is supplied by Beckman.

TAME assay employs p-tosyl-L-arginine methyl ester.

t-Butyl methyl ether was purchased from Aldrich Chemical Co. (Milwaukee, Wis.).

TFA stands for trifluoroacetic acid and was purchased from Pierce (Rockford, Ill.).

Thioanisole was purchased from Aldrich Chemical Co. (Milwaukee, Wis.).

TPCK stands for L-1-chloro-3-[4-tosylamido]-4-phenyl-2-butanone and is available from Sigma Chemical Co. (St. Louis, Mo.).

Tris stands for tris-(hydroxymethyl)aminomethane and was purchased from the Sigma Chemical Co. (St. Louis, Mo.).

Triton X-100 was purchased from the Sigma Chemical Co. (St. Louis, Mo.).

TRT stands for the trityl group.

Turbochrome Chromatography Software is used with the amino acid analyzer, peptide synthesizer, and protein sequencer and is available from P. E. Nelson (Cuppertino, Calif.).

Undansylated VIP was purchased from Sigma (St. Louis, Mo).

Vydac C-18 reverse phase HPLC column (2.2×25 cm) was obtained from Vydac, Hesperia, Calif.

Amino acids and other peptide synthesis reagents besides those listed above were obtained from Applied Biosystems (Foster City, Calif.).

EXAMPLE 1

Peptide Synthesis

Dansylated VIP (28 amino acids) was synthesized on an Applied Biosystems model 430A peptide synthesizer using NMP-HBTU Fmoc chemistry. The side chain protecting groups used were: TRT for asparagine and aspartic acid; t-butyl for serine, tyrosine, and threonine; BOC for lysine; and PMC for arginine. The peptide was synthesized on rink resin, with the dansyl-histidine coupled as the final N-terminal amino acid. Cleavage and deprotection was performed in 88% TFA, 4% thioanisole, 2% ethanedithiol, 4% liquefied phenol, and 2% $H_2O$ for 2 hours at room temperature. The crude peptide was precipitated with t-butyl methyl ether, centrifuged at 3000 RPM in a Sorval® RT 6000D model table top centrifuge for 5 minutes and washed twice in t-butyl methyl ether. Product dansyl-VIP (Dns-VIP) was purified by reverse-phase HPLC using a Vydac C-18 reverse phase column (2.2×25 cm). Purification was achieved using an isocratic separation with 28% ACN, 0.1% TFA, at a flow rate of 10 ml/min. Under these conditions, dansyl-VIP eluted as a single peak with a retention time of 12.5 minutes. The purified material was lyophilized and stored at −20° C. until needed. The peptide was dissolved in 0.1% TFA to achieve a stock peptide concentration of 1 mM. The composition and concentration of dansyl-VIP was determined by amino acid analysis. Samples were hydrolyzed under argon in the vapor phase using 6 N hydrochloric acid with 2.0% phenol at 160° C. for 2 hr. PTC amino acid analysis was performed on an Applied Biosystems model 420A Derivatizer with on-line model 130A Separation System and Turbochrome Chromatography Software. Data was normalized to the known composition of VIP. See Mutt, Ann. NY Acad. Sci., 527, 1–20 (1988).

EXAMPLE 2

Purification of Human Lung Tryptase

Mast cell tryptase was purified to homogeneity from fresh human lung samples with minor modifications to the published procedure of Smith, T. J., Hougland, M. W., and Johnson, D. A., J. Biol. Chem., 259, 11046–11051 (1984). All steps were performed at 4° C. Briefly, 400 g of frozen or fresh human lung was cut into approximately 1 cm square pieces, placed in a Waring blender with 500 ml of ice-cold water, blended for 1 min. on a setting of 1, then centrifuged for 20 min. at 10,000×g. The resulting pellet was then blended in 500 ml of low salt buffer, then centrifuged again as above. This procedure was repeated 5 times to remove blood and other contaminants. After the last centrifugation, tryptase was extracted from the pellet by blending in 500 ml of high salt buffer for 2×2 min. on a blender setting of 7. The sample was then centrifuged as above and the high salt extraction was repeated. The resulting supernatants, containing the tryptase, were pooled and filtered through cheese cloth to remove fat particles. Cetylpyridinium chloride 0.09 % (wt/vol) was added after the high salt extraction. Next, an ammonium sulfate precipitation was performed. Solid ammonium sulfate was added to the crude high salt extract to a final concentration of 45% saturation (on ice). After 20 min. the sample was centrifuged at 20,000×g for 30 min. The "pellet" floated to the surface due to the high density of the crude extract and was removed by carefully decanting the supernatant and filtering it through cheese cloth. The supernatant containing the tryptase was further purified by hydrophobic interaction chromatography using octyl-sepharose. The 45% ammonium sulfate supernatant was batch absorbed to octyl-sepharose (200 ml) equilibrated in 45% ammonium sulfate (Buffer A). The resin was poured into a column (5×10 cm), washed with 10 column volumes of Buffer A (2 ml/min.) and eluted with a linear gradient (200 ml each) into 10 mM MES (pH 6.1)(Buffer B). Tryptase activity was monitored using the GPK-AMC assay as described below. The active fractions were pooled and diluted with ice-cold water to a conductivity of 29 mmho. The sample was immediately loaded onto a heparin agarose column (20 ml) prepared according to Schwartz, L. B., J. Immunol., 134, 526–531 (1984), equilibrated in 10 mM MES (pH 6.4) plus 0.1 M NaCl at a flow rate of 1 ml/min. The column was washed with 10 mM MES (pH 6.1) plus 10% glycerol, and tryptase was eluted with a linear gradient into the same buffer plus 1M NaCl (100 ml each). Fractions (1 ml) were collected into test tubes containing heparin (10 µg/ml final). Active fractions were pooled, concentrated by Centriprep 10 (Amicon) and stored at −80° C. until use. Tryptase concentration was determined by the absorbance at 280 nm using the extinction coefficient from Smith et al. (above).

Protein purity was determined by silver staining of reducing 10–20% SDS-PAGE tricine buffered gels that were run according to the manufacturer's specifications. The purified tryptase was homogeneous as judged by silver staining. The band appeared diffuse with a molecular weight centered around 31,000 g/mole. This same band reacted in a Western blot analysis using the A2 anti-tryptase monoclonal antibody (from Dako Inc.) at a 1:500 dilution according to the manufacturer's specifications. The specific activity of the protein was 97 U/mg in the TAME assay, which is comparable to previously reported values of Smith, above [1 U=1 micromole product formed per minute].

EXAMPLE 3

GPK-AMC Assay for Tryptase Activity Measured in a 96-Well Microtiter Plate

Tryptase activity was measured according to the procedure of Schwartz, et al., J. Biol. Chem., 261, 7372–7379 (1986), with minor modifications, using Gly-Pro-Lys-Aminomethylcoumarin (GPK-AMC) as a substrate. The reaction was performed in assay buffer (0.1M Tris, pH 8.0, 10 µg/ml heparin) at room temperature in a 96-well microtiter plate (Perkin-Elmer, Norwalk, Conn.). The amount of coumarin produced by tryptase was determined by measuring the fluorescence (ex=372 nm, em=432 nm) on a Perkin-Elmer LS-50B fluorimeter equipped with a plate reader. 50 µl of tryptase (final concentration of 333 pM) was mixed with either 50 µl of the sample to be tested or with assay buffer and incubated for 5 min. at room temperature. The reaction was started by the addition of 50 µl of the substrate GPK-AMC in assay buffer plus 0.5% DMSO (final concentration of substrate was 33 µM). The fluorescence intensity was measured every 5 minutes. For samples that were being tested for modulators of tryptase activity, the % inhibition for each fraction was determined by:

$$\% \text{ inhibition} = 100 \times [1 - F0/F1]$$

where F0 is the fluorescence of the unknown and F1 is the fluorescence of the tryptase-only control. One unit of activity for the inhibitors is defined as the amount needed to achieve 50% inhibition in the assay using the conditions as described.

EXAMPLE 4

VIP Assay for Tryptase Activity

Isolation of VIP fragments

A reaction mixture consisting of 0.5 mg of dansyl-VIP, 0.6 µg tryptase in 100 mM Tris-HCl, pH 7.8, containing 10 µg/ml heparin was incubated at 37° C. for 30 minutes. The reaction was stopped by the addition of TFA to a final concentration of 3% (v/v). Approximately 95% of the full length peptide was cleaved at this time and the products were purified using C-18 reverse-phase chromatography (Vydac column, 5 micron, 0.46×25 cm) by elution with a linear gradient of 20–35 % ACN (plus 0.1% TFA) over 20 minutes (25° C., 1 ml/min). Chromatography was performed using a Beckman HPLC equipped with a model 168 diode array detector and System Gold software. Absorbance peaks (215 nm) were collected, concentrated by a Speed Vac concentrator (Savant, Farmingdale, N.Y.), and characterized. Purified dansyl-VIP fragments (1-14 and 1-20) were used to generate calibration curves, discussed below.

Figure 1:
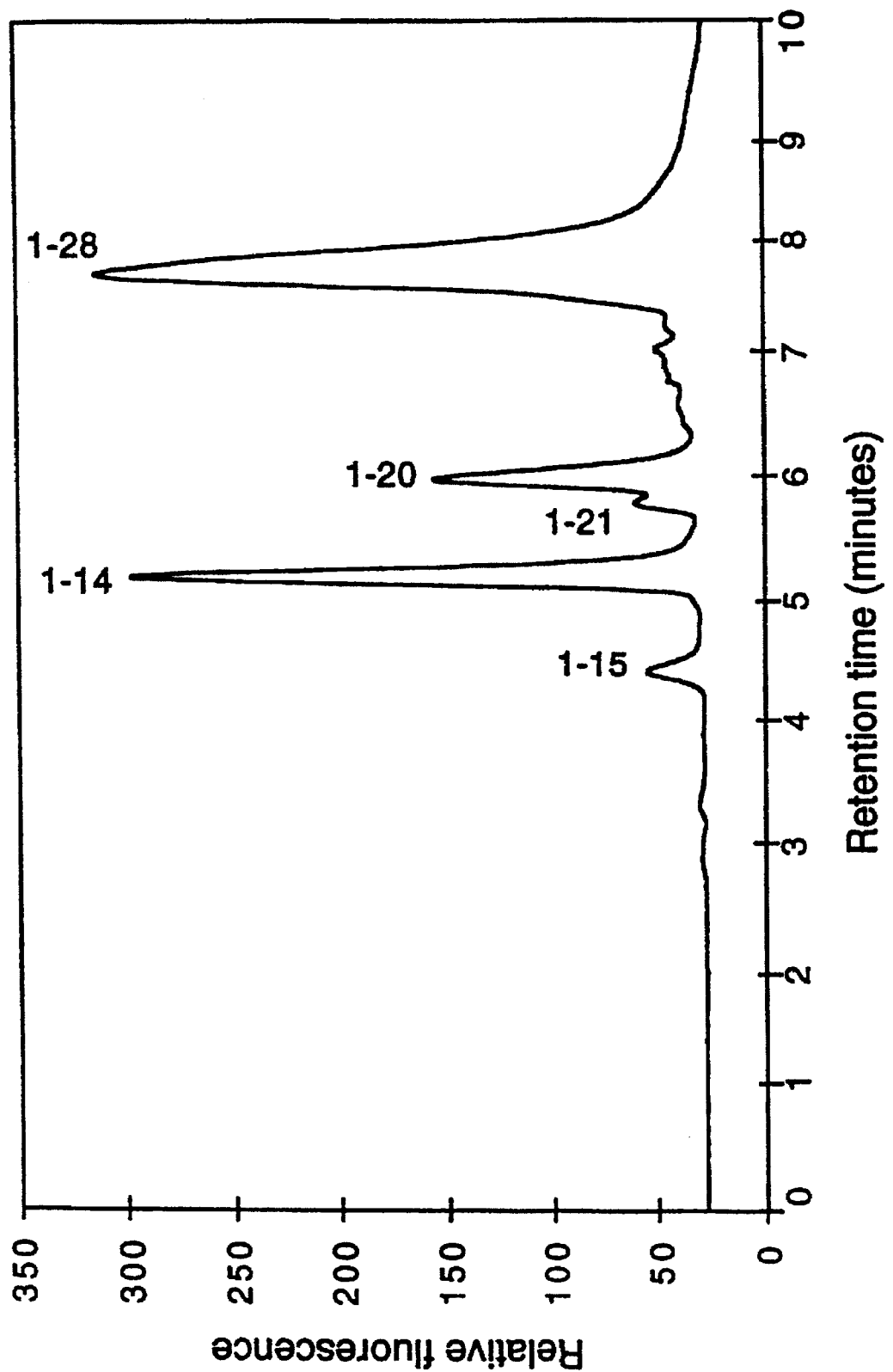
FIG. 1 is an HPLC elution profile of the enzymatic digest of Dns-VIP by human mast cell tryptase, showing separation of VIP fragments consisting of amino acids 1-14, 1-15, 1-20, and 1-21 from full-length VIP (1-28)

FIG. 1 shows that incubation of Dns-VIP with human lung tryptase results in the formation of two major and two minor peptide fragments, which were subjected to amino acid analysis and mass spectrometry. The major peptide fragments were identified as Dns-VIP-(1-14) and Dns-VIP-(1-20) respectively, and the two minor peptide fragments were identified as Dns-VIP-(1-15) and Dns-VIP-(1-21) respectively. The Dns-VIP-(1-21) material elutes as a shoulder on the Dns-VIP-(1-20) material. The following retention times were observed: Dns-VIP-(1-14), 5.4 min; Dns-VIP-(1-15), 4.6 min; Dns-VIP-(1-20), 6.1 min; Dns-VIP-(1-21), 6.0 min; Dns-VIP, 7.9 min.

Figure 2:
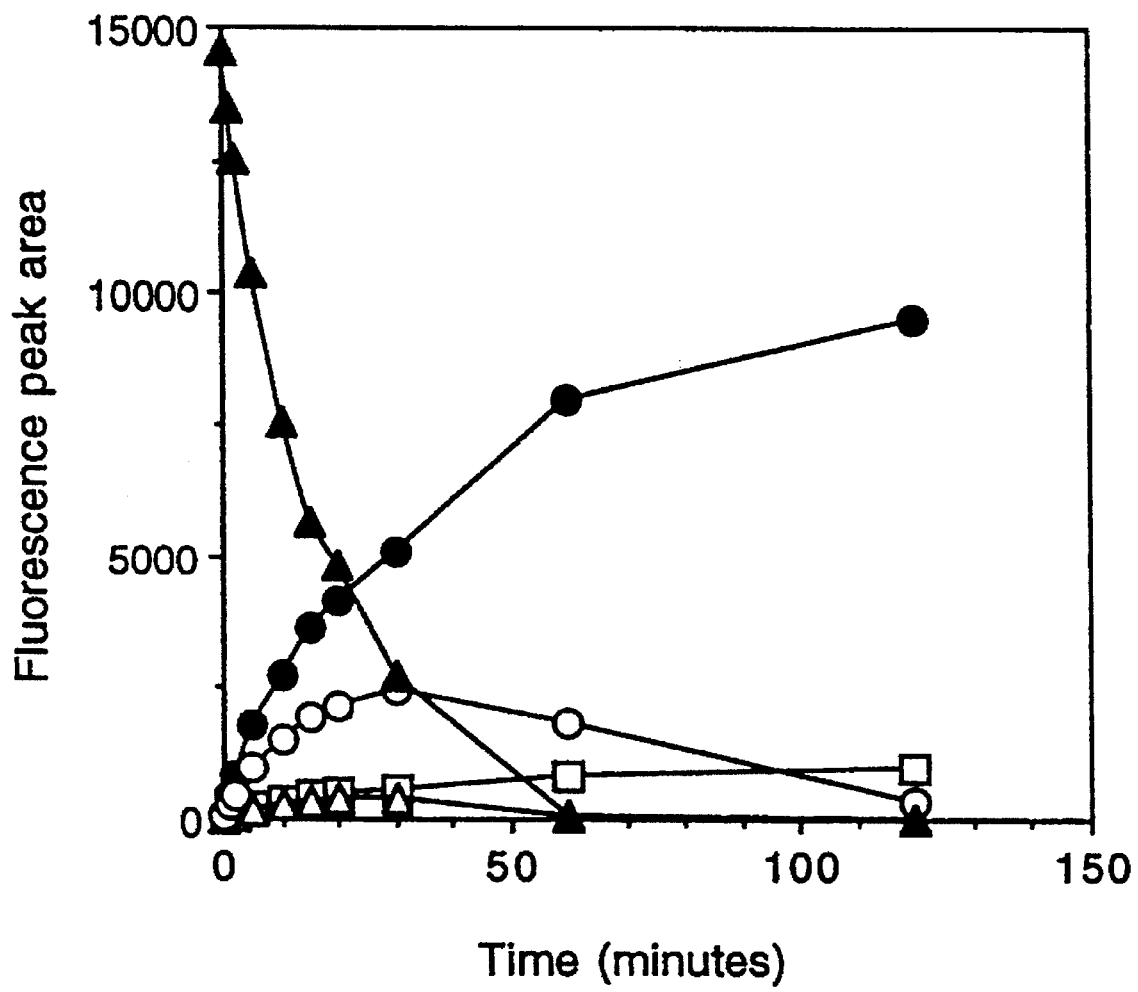
FIG. 2 is a plot of the time course of formation/disappearance of Dns-VIP-(1-14) (closed circles), Dns-VIP-(1-15) (open squares), Dns-VIP-(1-20) (open circles), Dns-VIP-(1-21) (open triangles), and Dns-VIP (closed triangles) upon enzymatic digestion of Dns-VIP by human mast cell tryptase.

FIG. 2 shows the time course of the formation/disappearance of Dns-VIP-(1-14) (closed circles), Dns-VIP-(1-15) (open squares), Dns-VIP-(1-20) (open circles), Dns-VIP-(1-21) (open triangles), and Dns-VIP (closed triangles). The data show that the product-precursor kinetics for the accumulation of the VIP fragments was consistent with initial cleavage of VIP occurring after Arg-14 and Lys-20, with similar rates. Once the full-length Dns-VIP was exhausted, the Dns-VIP-(1-20) was further degraded to the Dns-VIP-(1-14). After complete digestion with tryptase, the final (stable) dansyl product was predominantly Dns-VIP-(1-14), with some Dns-VIP-(1-15), and a small amount of Dns-VIP-(1-20) also present. No fragments derived from cleavage after the arginine residue at position 12 were detected. No measurable N-Dansylated products were formed in the absence of added enzyme over a two hour period.

Generation of Standard Curves for Dns-VIP, Dns-VIP-1-14), and Dns-VIP-(1-20)

To determine the amount of each product as well as the amount of substrate remaining, standard curves were generated by injecting purified Dns-VIP-(1-14) and Dns-VIP-(1-20) (0.5 to 200 pmoles) as well as Dns-VIP (20 to 1000 pmoles). The following equations were used to convert fluorescence peak area into pmoles of peptide: for Dns-VIP, y=34.8+36.5 x; for Dns-VIP-(1-14), y=29.3+20.2 x; for Dns-VIP-(1-20), y=0.63+33.0 x, where y is the fluorescence peak area and x is the pmoles of peptide injected onto the column. Correlation coefficients were greater than 0.997 in all cases. As little as 0.5 pmoles of Dns-VIP-(1-14) and Dns-VIP-(1-20) could be detected under the conditions employed.

Measurement of the Initial Rate of VIP Hydrolysis

In a typical assay, mast cell tryptase (12.5 pM) was incubated at 37° C. with dansyl-VIP (0.2-2 µM) in 100 mM Tris-HCl (pH 8.0) containing 1 µg/ml porcine mucosal heparin and 0.02% Triton X-100 in a final volume of 2.0 ml. To some samples, secretory leukocyte protease inhibitor was added to a final concentration of between 0 and 107 nM. The tryptase was pre-incubated with the SLPI, if added, for 5 min. at 37° C. before initiating the reaction by the addition of Dns-VIP. Aliquots (250 µl) were removed at 0, 2.5, 5.0, 7.5, 10, and 20 minutes to micro-vials (Sunbrokers) and the reaction terminated by the addition of TFA to a final concentration of 3% (v/v). The acidified reaction mixture was subjected to chromatography on a C-18 reverse-phase column (Vydac, 5 micron, 0.46×25 cm). Peptide hydrolysis was monitored by HPLC using a Hewlett Packard HP1090 unit complete with binary solvent delivery and autoinjection capability. Fluorescent detection (postcolumn) was performed with an inline Gilson Model 121 filter fluorimeter (excitation at 310–410 nm, emission at 480–520 nm). Dns-VIP fragments were separated from any unconverted Dns-VIP using a linear gradient of 69:31 (v/v) to 50:50 (v/v) C:D over 5.5 minutes (C=100 mM sodium acetate, pH 6.5 plus 0.2% sodium azide, D=80% ACN in water), with return to 69:31 (v/v) C:D at 6.5 minutes. Chromatography was performed at 1.0 ml/min at 25° C. The N-terminal fluorescent products were identified by subjecting known VIP fragments (see above) to chromatography under identical conditions.

Kinetic Parameters for Dns-VIP Degradation

The kinetic parameters $K_m$, kcat, and Vmax for the initial rate of formation of Dns-VIP-(1-14) and Dns-VIP-(1-20), as well as the initial rate of disappearance of full-length Dns-VIP were determined. Results are shown in Table III. The initial velocity for the formation of Dns-VIP-(1-20) also contains the rate for the formation of Dns-VIP-(1-21) since it appears as a shoulder on the Dns-VIP-(1-20) peak within the elution profile. A $K_m$ value of 0.1 µM was observed for the formation of both Dns-VIP-(1-14) and Dns-VIP-(1-20) while a $K_m$ value of 0.5 µM was observed for the disappearance of Dns-VIP. Tryptase was shown to have a slight preference for hydrolysis after Arg-14 over Lys-20, demonstrating a kcat/$K_m$ that is almost two-fold higher. The effect of salt concentration on the initial rates of cleavage of Dns-VIP was measured in 150 mM NaCl and 10 mM $CaCl_2$. In all cases, the kcat/$K_m$ values decreased with increasing salt concentration. In 150 mMNaCl there was a 9-fold decrease in the kcat/$K_m$ ratio for the disappearance of Dns-VIP and a 16-fold and 47-fold decrease for the formation of Dns-VIP-(1-14) and Dns-VIP-(1-20) respectively. Interestingly, all the Vmax values increased in 150 mM NaCl, with the largest being a 4-fold increase in the rate of formation of Dns-VIP-(1-14). However, this effect was offset by an increase in all of the $K_m$ values. $K_m$ for Dns-VIP increased 14-fold whereas the value for Dns-VIP-(1-14) and Dns-VIP-(1-20) increased 59- and 72-fold respectively. The results for 10 mM $CaCl_2$ were similar in that $K_m$ and Vmax values increased and kcat/$K_m$ ratios decreased. The kcat/$K_m$ ratio for Dns-VIP disappearance decreased almost 5-fold while the ratio for the formation of Dns-VIP-(1-14) and Dns-VIP-(1-20) decreased 9-fold and 11-fold, respectively.

Data Analysis for VIP Assay.

Initial reaction velocities were obtained from a linear least squares analysis of the linear part of a plot of the number of picomoles of each product produced vs. time and where less than 10% of the total Dns-VIP was consumed. To determine the $K_i$ value, a Dixon plot of the form 1/V vs. [I] was made for data collected at two different concentrations of VIP, where V is the velocity (pmoles/min) and [I] is the concentration of SLPI used.

TABLE III

| | Kinetic Parameters for Enzymatic Cleavage of Dns-VIP | | | | | | | | |
|---|---|---|---|---|---|---|---|---|---|
| | $K_m$ (μM) | | | $V_{max}$ (pmol/min/mg) | | | kcat/Km ($M^{-1}$ $sec^1$ × $10^7$) | | |
| Addition | | | | | | | | | |
| Sequence | 1-28 | 1-14 | 1-20 | 1-28 | 1-14 | 1-20 | 1-28 | 1-14 | 1-20 |
| None | 0.5 | 0.1 | 0.1 | 4.3 | 1.3 | 0.6 | 1.8 | 2.3 | 1.4 |
| 150 mM NaCl | 7.4 | 7.7 | 9.4 | 6.6 | 4.9 | 1.1 | 0.2 | 0.14 | 0.03 |
| 10 mM $CaCl_2$ | 4.7 | 4.1 | 4.5 | 8.2 | 4.5 | 2.6 | 0.4 | 0.25 | 0.13 |

EXAMPLE 5

Identification of SLPI as a Tryptase Inhibitor in Nasal Secretions

Partial Purification of Tryptase Inhibitor Using Reverse-Phase Chromatography

Figure 3:
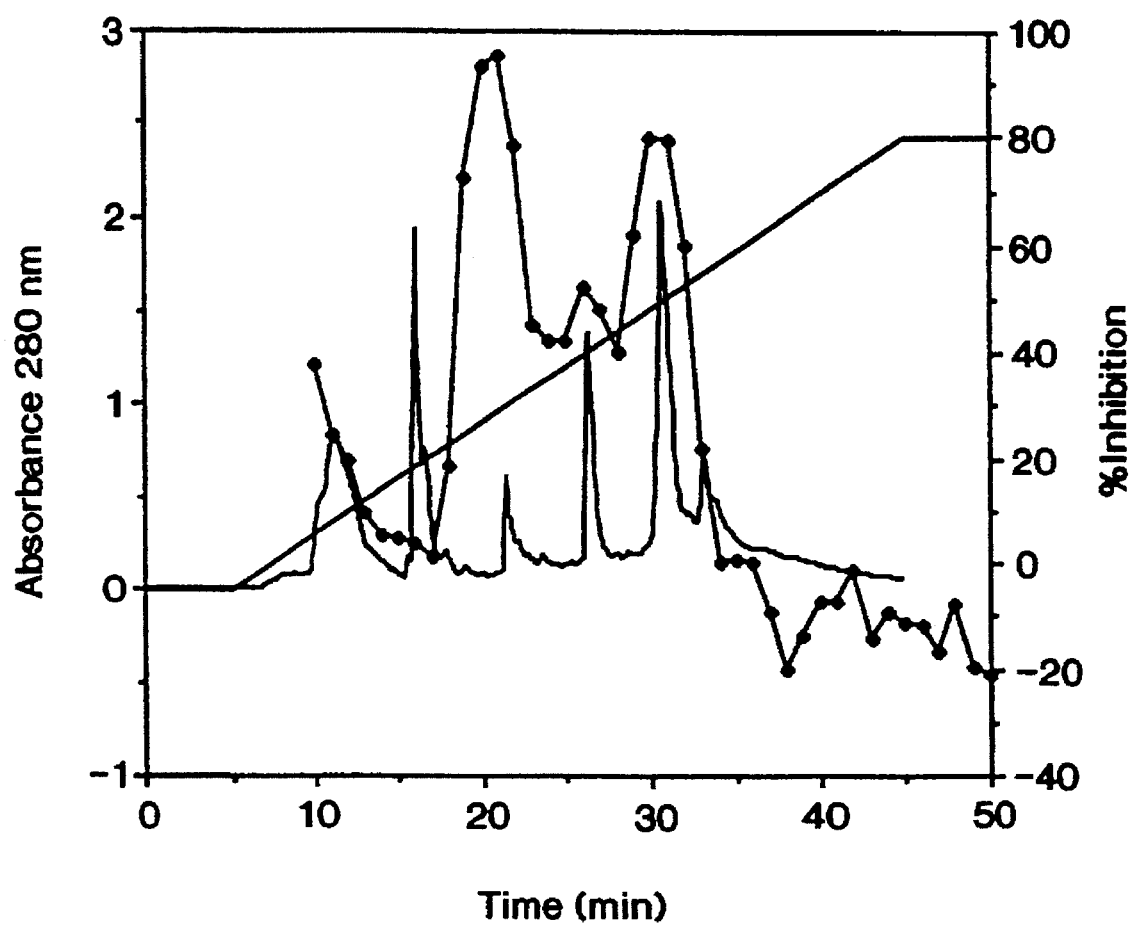
FIG. 3 is the HPLC elution profile from a reverse phase C-18 column purification of crude nasal secretions, showing absorbance at 280 nm (left axis, solid line), the % inhibition in the GPK-AMC assay (right axis, solid diamonds), and the gradient.

Nasal secretions were isolated from a person with chronic sinusitis. Samples (usually 2–15 ml) were frozen at –20° C. immediately after harvesting and stored frozen until needed (less than 6 months). For analysis, approximately 5 ml of frozen nasal secretions were thawed and subsequently extracted with 10 volumes of 0.1% TFA (at room temperature) by vortexing intermittently over a 5 minute period. Insoluble material was removed by centrifugation at 10,000×g for 30 min. The supernatant was then filtered through a 0.45 μM filter. 5 ml of crude extract was subjected to reverse phase chromatography on a Vydac C18 column (0.96×25 cm), where Buffer E was 0.1% TFA in water and Buffer F was 0.1% TFA in ACN. The chromatography was carried out at 2 ml/min with a wash of 0% F for 5 min. after injection followed by a gradient of 0–80% F over 40 minutes, using a Beckman model 126 HPLC with the System Gold software. The absorbance of the effluent at both 215 and 280 nm was monitored using a diode array model 168 detector. FIG. 3 shows the elution profile and the inhibitory activity of the various fractions. There are 2 peaks of inhibition at a retention time of 20 and 30 minutes, respectively, with a shoulder between them at approximately 25 minutes. Additional 5 ml aliquots were subjected to the same procedure until all of the crude extract was processed. 2 ml fractions were collected and a 200 μL aliquot was dried down in a Savant Speed Vac at room temperature. Once dry, the fractions were resuspended in 50 μL of 0.1M tris (pH 8.0) plus 10μg/ml heparin (porcine mucosa) and assayed in the GPK-AMC assay using a 96 well microtiter plate as described above.

Affinity Purification of Tryptase Inhibitory Activity on Anhydrotrypsin Sepharose The pooled fractions corresponding to the peak of FIG. 3 having a retention time of 20 min. were subjected to affinity chromatography on anhydrotrypsin sepharose. The samples were lyophilized and then resuspended in 0.1% TFA. The pH of the sample was raised to 8.0 with the addition of solid Tris base. $CaCl_2$ was added to a final concentration of 20 mM. The sample was then loaded onto the anhydrotrypsin-sepharose column equilibrated in 0.1M Tris buffer (pH 8.0) plus 20 mM $CaCl_2$ at a flow rate of 1 ml/min, and then washed with 10 ml of the same buffer. The column was then eluted with 200 mM NaAc (pH 4.0) plus 20 mM $CaCl_2$. The eluted material was concentrated in a Centricon-3 concentrator at 5,000×g (Amicon, Beverly, Mass). The sample was diluted 10 fold with 10 mM Tris (pH 8.0) and again concentrated to 100 μL. Subsequently the sample was dialyzed vs. 0.01% SDS using dialysis tubing (Spectrum, Gardena, Calif.) with a 1 kD MWCO. The pellet was resuspended in 40 μl of 3X sample buffer (Novex, San Diego, Calif.) plus 2-mercaptoethanol, heated at 100° C. for 5 min. and subjected to SDS-PAGE on a 10–20% acrylamide, tricine buffered gel (Novex). After electrophoresis, the protein(s) were transferred to a Problott membrane following standard protocols and protein was visualized by staining with 0.1% Coomassie blue in 50% methanol. The blot was destained in 50% methanol and then air dried. One species was visible at 16 kD. This band was cut out of the blot and the protein sequences were determined with an Applied Biosystems model 477A Protein Sequencer operated in the gas phase with on-line model 120A Analyzer and PE Nelson Turbochrom Software. This N-terminal sequence analysis identified the species as a proteolytically modified form of human SLPI. The identified sequences are as follows:

1°: Xaa-Leu-Asn-Pro-Pro-Asn-Phe-Xaa-Xaa-Xaa- [SEQ ID NO: 17]

2°: Xaa-Gly-Lys-Xaa-Phe-Lys-Ala-Gly-Val-Xaa- [SEQ ID NO: 18].

The primary sequence corresponds to an internal proteolytic cleavage within the molecule after position 72 and the secondary sequence corresponds to mature N-terminus of SLPI.

Affinity Purification of Tryptase Inhibitory Activity on a Tryptase Affinity Column The tryptase inhibitory activity that was identified in crude nasal secretions was also purified on a tryptase affinity column. Tryptase was purified to homogeneity from human lung as described above. To immobilize the tryptase for the affinity chromatography, heparin sepharose was used. 80 μL of a 1 mg/ml solution of tryptase was made 2M NaCl to dissociate the heparin already bound to the molecule. Heparin-sepharose was prepared by swelling enough powder in deionized water to make 4 ml of resin. The swelled resin was equilibrated in column buffer consisting of 10 mM MES (pH 6.1), 10% glycerol, and 0.02% Triton X-100. The tryptase solution (80 μl) that contained 2M NaCl was added to the resin and the total volume adjusted to 10 ml by addition of more column buffer. The sample was mixed overnight at 4° C. to allow the tryptase to bind to the heparin on the resin. A one ml column was prepared from an aliquot of this slurry and washed with 10 ml. of column buffer.

Crude nasal secretions were prepared as described above. 12 ml of crude extract (in 0.1% TFA) was adjusted to a pH of 8.05 by the addition of Tris base. All steps were performed at room temperature. The sample was centrifuged at 10,000×g for 30 min. and the supernatant filtered through a 0.22 μm filter. 10.5 ml of a 2.62 mg/ml solution of the filtered extract was loaded onto the one ml tryptase affinity column at less than 1 ml/min. The column was washed with 75 ml of column buffer until the O.D. at 280 nm of the effluent was less than 0.01. Bound proteins were eluted with 0.1M formic acid at pH 1.7. One ml fractions were collected and immediately neutralized with tris base. Fractions 1 and 2 were pooled together and dialyzed vs. 1 L of 20 mM ammonium bicarbonate using dialysis tubing with a MWCO of 1,000 g/mole. The sample was dialyzed overnight with one change of buffer. After dialysis, the sample was dried in a Speed Vac concentrator and then resuspended in 1X sample buffer (0.45M Tris (pH 8.5), 2.25% SDS, 10% glycerol plus 2.5% BME) for SDS-PAGE analysis on 10–20% acrylamide gels (Novex).

Amino Acid Sequence Determination of Tryptase Affinity Purified Material

The proteins that were affinity purified on a tryptase column were subjected to SDS-PAGE analysis using 10–20 % acrylamide gels (Novex) and run according to the manufacturer's directions. The Problott membrane was stained with Coomassie blue and revealed four species with molecular weights of approximately 55, 13, 9.5, and 9 kD by comparison with Bethesda Research Labs' low molecular weight standards. The bands were excised from the membrane and subjected to N-terminal sequence analysis as described above. The sequence of the N-terminus of the 13 kD species was determined to be 1° : Xaa-Gly-Lys-Xaa-Phe-Lys-Ala-Gly-Xaa-Xaa- [SEQ ID NO: 19]. This sequence corresponds to the N-terminus of secretory leukocyte protease inhibitor (SLPI).

EXAMPLE 6

Inhibition of Tryptase by Recombinant SLPI

Figure 4:
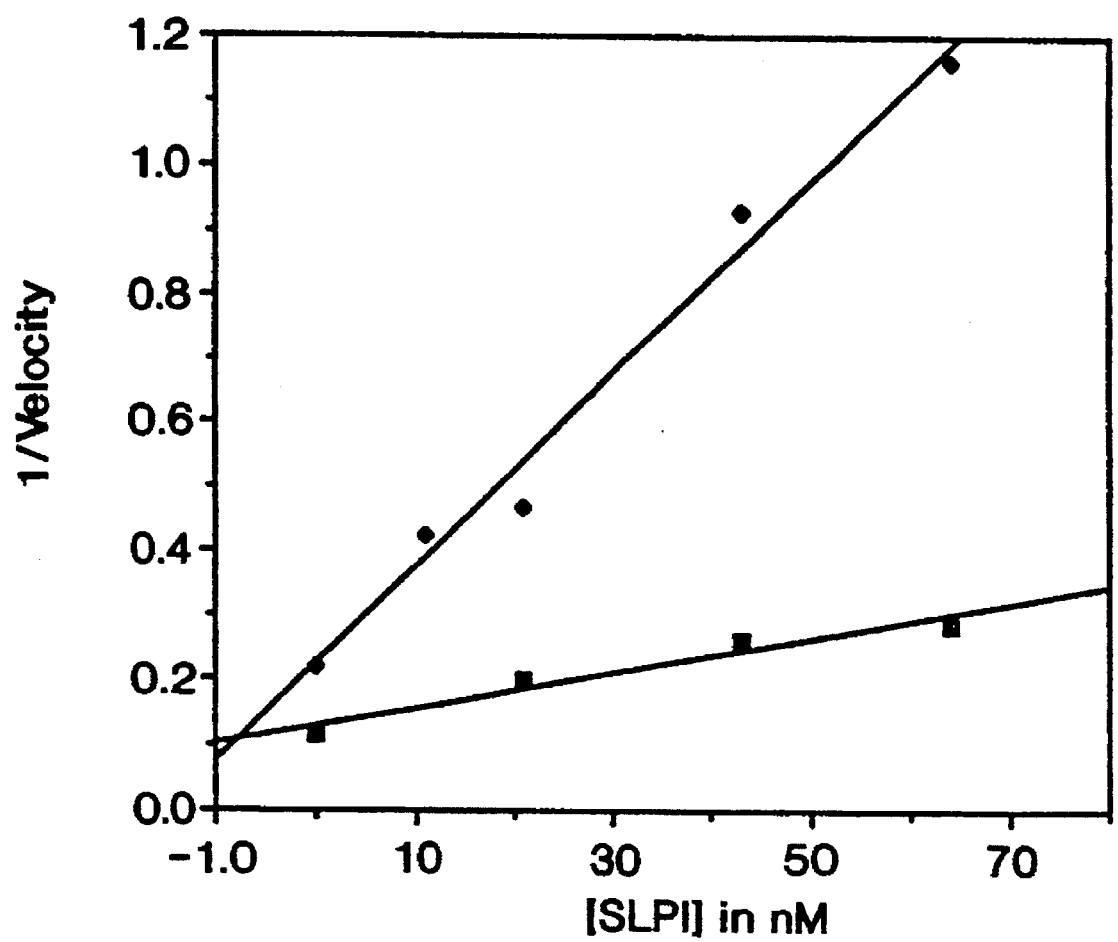
FIG. 4 shows the Dixon plot for the inhibition of tryptase by recombinant SLPI in the VIP assay using both 0.2 (diamonds) and 0.8 (squares) μM VIP, the rate of loss of the full-length VIP (1-28) being monitored.

FIG. 4 shows inhibition by SLPI of the proteolytic activity of tryptase using Dns-VIP as a substrate. From this Dixon plot, tryptase appears to be a competitive inhibitor and the $K_i$ value for the inhibition of the degradation of the full length peptide was determined to be 8 nM. This shows that SLPI is a potent inhibitor of tryptase and is the first demonstration of tryptase inhibition by a biological serine protease inhibitor. Accordingly, SLPI provides a non-toxic, non-immunogenic tryptase inhibitor for prevention or amelioration of mast-cell mediated diseases. The novel fragments and muteins of SLPI which retain the inhibitory activity of SLPI will provide similar advantages and can be engineered to have advantages such as extended half-life, increased potency, and improved pharmacological profiles.

EXAMPLE 7

Cleavage of SLPI into N- and C-Terminal Domains

Formic Acid Cleavage of SLPI

Following published protocols of Van-Seuningen and Davril, Biochem. and Biophys. Res. Commun., 179, 1587–1592 (1991), SLPI was cleaved into two separate domains using acid cleavage of the Asp-Pro bond located at position 49-50. Recombinant SLPI was cleaved by reacting 1.3 mg of SLPI in 0.26 ml 70% formic acid for 1 week at 40° C. The mixture was then dried in a Speed Vac concentrator. Any residual acid was removed by dissolving the sample in 0.25 ml deionized water and drying in the Speed Vac and then repeating this process. The final dried product was resuspended in 0.1 ml of 0.1% TFA in water.

Purification of the SLPI domains

Figure 5:
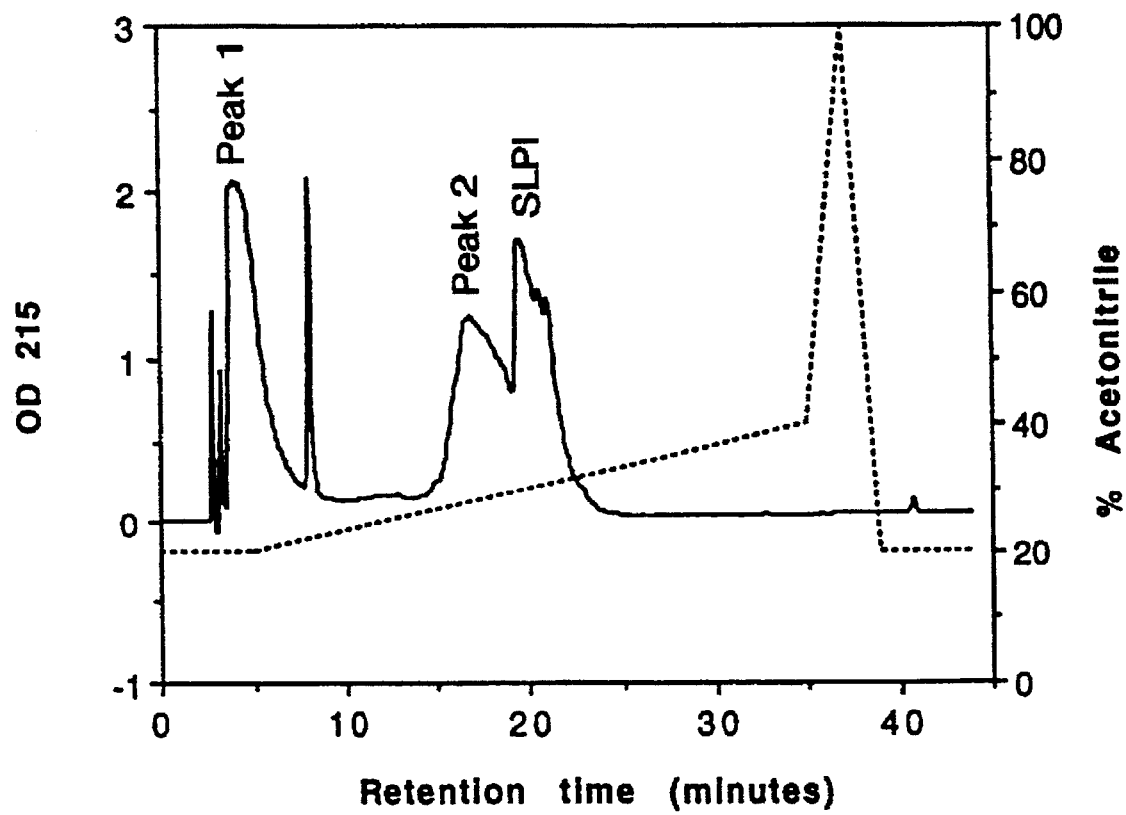
FIG. 5 shows the HPLC elution profile of acid treated SLPI from a C-8 reverse-phase column, absorbance at 215 nm (solid line) and the elution gradient (dashed line) being plotted vs. retention time.

The N-terminal and C-terminal domains of SLPI were separated using C-8 reverse-phase chromatography (Vydac, 5 micron, 0.46×25 cm). Protein was eluted with a linear gradient of 20–40% ACN in 0.1% TFA over 30 minutes (25° C., 1 ml/min). Chromatography was performed using a Beckman HPLC equipped with a model 168 diode array detector and System Gold software. The separation yielded 3 major peaks, shown in FIG. 5. The first peak (peak 1) eluted in the void fractions (20% ACN) and the second peak (peak 2) eluted at 31% ACN. A third peak, eluting at 33% ACN, had the same retention time as full-length recombinant SLPI that had not been subjected to acid treatment. Fractions corresponding to peaks 1 and 2 were separately pooled and then further purified using C-18 reverse-phase chromatography. Results are shown in FIGS. 6A and B respectively. Peak 1 from FIG. 5 (the C-8 elution, 4.6 ml) was diluted 1:1 with 0.1% TFA in water and loaded directly onto the C-18 column (Vydac, 5 micron, 0.46×25 cm). The protein was eluted in a single major peak at 23% ACN using a linear gradient of 10 to 40% ACN in 0.1% TFA over 40 minutes (FIG. 6A). This peak (215 nm) was collected and lyophilized. Peak 2 from FIG. 5 (C-8 column) was lyophilized and resuspended in 0.1 ml of 0.1% TFA prior to chromatography on C-18 under identical elution conditions as for peak 1. The major peak (215 nm) from this sample eluted from the C-18 column at 29% ACN (FIG. 6B), and was collected and lyophilized.

Characterization of the Purified N- and C-terminal Domains of SLPI

Amino acid analyses of the purified SLPI fragments (from FIG. 6) were performed on an Applied Biosystems 420A derivatizer with an inline model 130A HPLC using 150 pmoles of the protein constituting the major peak of FIG. 6A and 74 pmoles of the protein constituting the major peak of FIG. 6B after hydrolysis of the samples for 2 hours at 160° C. The results were compared to the theoretical composition of the two SLPI domains where the N-terminal domain corresponds to amino acids 1-49 and the C-terminal domain corresponds to amino acids 50-107. The experimentally determined composition of material from FIG. 6A matched the composition of the N-terminal domain of SLPI with an accuracy of 97%. The experimentally determined composition of the material from FIG. 6B matched the C-terminal domain of SLPI with an accuracy of 90%, as shown in Table IV. The amino acid analysis shows 190 μg of the N-terminal domain (from FIG. 6A) and 47 μg of the C-terminal domain (from FIG. 6B) were obtained, for yields of 29% and 7%, respectively.

TABLE IV

Amino acid compositions of Peak 1 and Peak 2 isolated from the formic acid treatment of recombinant SLPI

| Amino acid residue | Peak 1 (Exp.) | $SLPI_{1-49}$[a] (Theoretical) | Peak 2 (Exp.) | $SLPI_{50-107}$[a] (Theoretical) |
|---|---|---|---|---|
| ASP | 2.6 | 3 | 4.7 | 6 |
| Glu/Gln | 3.2 | 4 | 3.4 | 3 |
| Ser | 3.6 | 4 | 2.4 | 2 |
| Gly | 4.1 | 4 | 6.0 | 5 |
| His | 0.0 | 0 | 0.1 | 0 |
| Arg | 2.0 | 2 | 3.0 | 3 |
| Thr | 1.0 | 1 | 2.8 | 3 |
| Ala | 2.0 | 2 | 1.0 | 1 |
| Pro | 5.0 | 5 | 7.4 | 8 |
| Tyr | n.d.[b] | 1 | 1.1 | 1 |

TABLE IV-continued

Amino acid compositions of Peak 1 and Peak 2 isolated from the formic acid treatment of recombinant SLPI

| Amino acid residue | Peak 1 (Exp.) | $SLPI_{1-49}$[a] (Theoretical) | Peak 2 (Exp.) | $SLPI_{50-107}$[a] (Theoretical) |
|---|---|---|---|---|
| Val | 1.1 | 1 | 3.5 | 4 |
| Met | 0.0 | 0 | 3.2 | 4 |
| Cys | n.d. | 8 | n.d. | 8 |
| Ile | 1.1 | 1 | 0.7 | 0 |
| Leu | 2.2 | 2 | 3.4 | 3 |
| Phe | 1.1 | 1 | 1.3 | 1 |
| Lys | 9.4 | 9 | 6.2 | 6 |
| Trp | n.d. | 1 | n.d. | 0 |

[a]The amino acid composition was deduced from the amino acid sequence of SLPI with cleavage occurring at the single $Pro_{49}$—$Asp_{50}$ bond.
[b]Tyrosine in Peak 1 was omitted due to an interfering buffer peak.
n.d.: not determined.

EXAMPLE 8

Inhibition of Tryptase by the N- and C-Terminal Domains of SLPI

Inhibition of Tryptase in the VIP Assay

Mast cell tryptase (final 12.5 pM tetramer) was incubated at 37° C. with the N-(1.4–1400 nM) or C-(0.3–300 nM) terminal domains of SLPI in 500 µl assay buffer (0.1M Tris, pH 8.0, 1 µg/ml heparin, 0.02% Triton X-100) for 5 minutes at 37° C. The reaction was initiated by the addition of either 0.4 or 0.8 µM dansylated-VIP. At 2.5 and 5.0 minutes a 250 µl aliquot was withdrawn and the reaction terminated by pipeting the solution into a microvial containing 25 µl 30% TFA. The assay conditions were as described above.

Data Analysis for VIP Assay

To determine the $K_i$ value for each fragment, a Dixon plot of the form 1/V vs [I] was made. These are shown in FIG. 7, and the results are listed in Table V. From the Dixon plots, the $K_i$ values for the inhibition of the formation of Dns-VIP-(1-14) by the N- and C-terminal domains were shown to be 130 nM and 1.6 nM, respectively (FIG. 7).

Inhibition of Tryptase in the GPK-AMC Assay

Inhibitory activity against tryptase and bovine trypsin was measured using Gly-Pro-Lys-aminomethylcoumarin as a substrate. The reaction was performed in assay buffer that consisted of 0.1M Tris (pH 8.0), 1 µg/ml heparin, 0.02% Triton X-100, with 20 mM $CaCl_2$ included only in the trypsin assays. The amount of coumarin produced was determined by measuring the fluorescence (ex=370 nm, em=432 nm) on a Perkin-Elmer LS-50B fluorimeter. To measure tryptase activity, 12 µl of a 1 nM solution of tryptase (tetramer) was incubated with either the N- (34 to 650 nM final) or the C-terminal (7–150 nM final) domain of SLPI in 1.0 ml of assay buffer for 5 minutes at 37° C. The reaction was started by the addition of the substrate GPK-AMC (20 or 40 µM final) and the increase in fluorescence was measured over a 2 minute period. In order to measure trypsin activity, 3.3 µl of a 10 µg/ml solution was incubated with either the N- or C- terminal domains of SLPI, and assayed using both 10 and 20 µM GPK-AMC. To determine $K_i$ values, Dixon plots of the form 1/V vs [I] were constructed. These are shown in FIG. 8, and the results are listed in Table V. The $K_i$ values for the inhibition of the tryptase catalyzed cleavage of GPK-AMC by the N- and C-terminal domains were determined to be 290 nM and 4.8 nM, respectively (FIG. 8).

In addition, the two domains of SLPI were able to inhibit the proteolytic activity of trypsin as measured by the GPK assay. The C-terminal domain inhibited trypsin with a $K_i$ value of 130 nM, while the N-terminal domain was unable to inhibit at a concentration of 1800 nM, as indicated in Table V. This result for the inhibition of trypsin is in agreement with previously published data.

TABLE V

Summary of $K_i$ values for the N- and C-terminal domains of SLPI for the inhibition of trypsin and tryptase

| | Trypsin | | Tryptase | | |
|---|---|---|---|---|---|
| | N-Term. SLPI | C-Term. SLPI | N-Term. SLPI | C-Term. SLPI | Full SLPI |
| GPK-AMC | $K_i \gg 1{,}800$ nM | $K_i = 130$ nM | $K_i = 290$ nM | $K_i = 4.8$ nM | * |
| VIP | N.D. | N.D. | $K_i = 130$ nM | $K_i = 1.6$ nM | $K_i = 8$ nM |

N.D. = not determined
*SLPI gives a biphasic response in this assay

Taken together, these results indicate that the N- and C-terminal domains of SLPI are potent inhibitors of tryptase activity as measured by both the GPK and VIP assays. Therefore, these fragments of SLPI should be useful for the treatment of asthma and other mast-cell mediated conditions.

EXAMPLE 9

Purification of Human Tryptase from Crude Lung Homogenates using Immobilized SLPI Preparation of Immobilized SLPI Resin 10 mg. of recombinant human SLPI is coupled to 5 ml of cyanogen bromide-activated sepharose prepared according to the manufacturer's specifications. The slurry is equilibrated by washing with at least 50 ml of 0.1M Tris (pH 8.0), 100 mM NaCl, 0.02% Triton X-100 (Buffer C). The resulting immobilized SLPI resin is then ready for use.

Affinity Purification of Tryptase 100 g of frozen or fresh human lung is cut into 1 cm square pieces, placed in a Waring blender with 100 ml of ice-cold water, and blended for 1 min. on a setting of 1. The material is next centrifuged for 20 min. at 10,000×g, then subjected to blending in 100 ml of low salt buffer and centrifuged again as above. Tryptase is extracted from the resulting pellet by blending in 100 ml of high salt buffer for 2×2 min. on a setting of 7, then centrifuging as above. The supernatant, containing the tryptase, is filtered through cheese cloth to remove fat particles. The filtrate is then mixed with 5 ml of immobilized SLPI resin (above). The sample is gently mixed for one hour at room temperature. The resin is poured into a column and washed with 100 ml of Buffer C at a flow rate of 1 ml/min. The tryptase is then eluted with 0.2M acetic acid (pH 4.0) at a flow rate of 0.5 ml/min. The pH of the eluted material is immediately raised to 7.0 by the addition of Tris base. Fractions containing tryptase activity are pooled and dialyzed vs. 10 AM MES (pH 6.1), 10% glycerol, 10 µg/ml heparin, 0.02% Triton X-100, and stored at −80° C. until used. The purity and activity of the enzyme are determined as discussed below.

EXAMPLE 10

Use of SLPI to Determine the Concentration of Tryptase in Crude Biological Sample The sample to be analyzed for tryptase is diluted appropriately in buffer containing 0.1M Tris (pH 8.0), 0.02%

Triton X-100, and 10 μg/ml heparin. A protease inhibitor cocktail is added including final concentrations of 0.5 mg/ml EDTA, 0.5 mg/ml E-64,100 μg/ml TPCK, and 0.7 μg/ml pepstatin. Various known concentrations of SLPI, dissolved in the same buffer, are added to the unknown and incubated at 37° C. for 10 min. in a total volume of 1 ml. The peptide substrate, Abz-His-Lys-Ala-Arg-Val-Leu-Xaa-Phe-Glu-Ala-Nle-Ser-NH$_2$ [SEQ ID NO: 20], wherein Xaa is p-nitro-Phe, is added to a final concentration of 14 μM. The increase in fluorescence at 420 nm is monitored with an excitation wavelength of 330 nm and 5 nm slit widths. The velocity of the reaction is measured over a 2 minute period. A plot of fractional tryptase activity remaining vs. the concentration of added SLPI is constructed. The data is analyzed using a non-linear least squares fit (Enzfitter, Biosoft, Ferguson, Mo.) to the equation below as described by Boudier and Bieth, Biochemica et Biophysica Acta., 995, 36–41 (1989):

$$a = 1 - ([E] + [SLPI] + (23 \times 10^{-9}) - \{([E] + [SLPI] + (23 \times 10^{-9}))^2 - 4[E][SLPI]\}^{1/2}) / 2[E]$$

where a is the fractional tryptase activity remaining, [SLPI] is the molar concentration of SLPI added to the reaction, and E is the unknown tryptase concentration. The least squares fit to the data allows the determination of the tryptase concentration. This method allows the determination of tryptase levels in such samples as bronchoalveolar lavage fluid, nasal secretions, blister fluid, urine, plasma, cell culture conditioned media and various tissue extracts.

Other embodiments of the invention will be apparent to the skilled in the art from a consideration of this specification or practice of the invention disclosed herein. It is intended that the specification and examples be considered as exemplary only, with the true scope and spirit of the invention being indicated by the following claims.

We claim:

1. A method of treating a mast cell-mediated condition in a mammal, which comprises administering to said mammal an amount of a pharmacologically active fragment of SLPI or mutein thereof which is effective to treat said condition, said fragment or mutein being selected from the group consisting of; the amino acid sequences 57-102 and 5-49 of human SLPI; the Leu-72-Arg and Leu-72-Lys muteins of the 57-107 and 57-102 sequences of human SLPI; the Leu-19-Arg and Leu-19-Lys muteins of the 5-49 sequence of human SLPI; the 5-102 sequence of human SLPI and muteins thereof; and muteins of a fragment of human SLPI wherein said mutein has the amino acid sequence Ser-Gly-Lys-Ser-Phe-Lys-Ala-Gly-Val-Cys-Pro Lys-Lys-Ser-Ala-Gln-Cys-Xaa-Leu-Arg-Tyr-Lys-Lys-Pro-Glu-Cys-Gln-Ser-Asp-Trp-Gln-Cys-Pro-Gly-Lys-Lys-Arg-Cys-Cys-Pro-Asp-Thr-Cys-Gly-Ile-Lys-Cys-Leu-Asp wherein Xaa is Arg or Lys.

2. A method of treating the conditions of asthma or allergic rhinitis in a mammal, which comprises administering to said mammal an amount of a pharmacologically active fragment or mutein of SLPI which is effective to treat said conditions, said fragment or mutein being selected from the group consisting of: the amino acid sequences 57-102 and 5-49 of human SLPI; the Leu-72-Arg and Leu-72-Lys muteins of the 57-107 and 57-102 sequences of human SLPI; the Leu-19-Arg and Leu-19-Lys muteins of the 5-49 sequence of human SLPI; the 5-102 sequence of human SLPI and muteins thereof; and muteins of a fragment of human SLPI wherein said mutein has the amino acid sequence Ser-Gly-Lys-Ser-Phe-Lys-Ala- Gly-Val-Cys-Pro-Lys-Lys-Ser-Ala-Gln-Cys-Xaa-Leu-Arg-Tyr-Lys-Lys-Pro-Glu-Cys- Gln-Ser-Asp-Trp-Gln-Cys-Pro-Gly-Lys-Lys-Arg-Cys-Cys-Pzo-Asp-Thr-Cys-Gly-Ile-Lys-Cys-Leu-Asp wherein Xaa is Arg or Lys.

3. A method of inhibiting tryptase, which comprises:

contacting tryptase with an amount of a pharmacologically active fragment or mutein of SLPI which is effective to inhibit the proteolytic activity of the tryptase, said fragment or mutein being selected from the group consisting of; the amino acid sequences 57-102 and 5-49 of human SLPI; the Leu-72-Arg and Leu-72-Lys muteins of the 57-107 and 57-102 sequences of human SLPI; the Leu-19-Arg and Leu-19-Lys muteins of the 5-49 sequence of human SLPI; the 5-102 sequence of human SLPI and muteins thereof; and muteins of a fragment of human SLPI wherein said mutein has the amino acid sequence Ser-Gly-Lys-Ser-Phe-Lys-Ala- Gly-Val-Cys-Pro-Lys-Lys-Ser-Ala-Gln-Cys-Xaa-Leu-Arg-Tyr-Lys-Lys-Pro-Glu-Cys- Gln-Ser-Asp-Trp-Gln-Cys-Pro-Gly-Lys-Lys-Arg-Cys-Cys-Pro-Asp-Thr-Cys-Gly-Ile-Lys-Cys-Leu-Asp wherein Xaa is Arg or Lys.

4. The method of claim 3, wherein said contacting step is conducted in a mammal manifesting a tryptase-mediated condition, for the purpose of treating said condition.

5. The method of claim 3 wherein said tryptase-mediated condition is one of the following: asthma and allergic rhinitis.

6. A peptide selected from the group consisting of the amino acid sequences 57-102 and 5-49 of human SLPI; the Leu-72-Arg and Leu-72-Lys muteins of the 57-107 and 57-102 sequences of human SLPI; the Leu-19-Arg and Leu-19-Lys muteins of the 5-49 sequence of human SLPI; the 5-102 sequence of human SLPI and muteins thereof; and muteins of a fragment of human SLPI wherein said mutein has the amino acid sequence Ser-Gly-Lys-Ser-Phe-Lys-Ala-Gly-Val-Cys-Pro- Lys-Lys-Ser-Ala-Gln-Cys-Xaa-Leu-Arg-Tyr-Lys-Lys-Pro-Glu-Cys-Gln-Ser-Asp-Trp- Gln-Cys-Pro-Gly-Lys-Lys-Arg-Cys-Cys-Pro-Asp-Thr-Cys-Gly-Ile-Lys-Cys-Leu-Asp wherein Xaa is Arg or Lys.

* * * * *

SEQUENCE LISTING ( 1 ) GENERAL INFORMATION:

( i i i ) NUMBER OF SEQUENCES: 21

( 2 ) INFORMATION FOR SEQ ID NO: 1:

( i ) SEQUENCE CHARACTERISTICS:
        ( A ) LENGTH: 49 amino acids
        ( B ) TYPE: amino acid
        ( D ) TOPOLOGY: linear ( i i ) MOLECULE TYPE:
        ( A ) DESCRIPTION:
            - Protein ( i i i ) HYPOTHETICAL: Yes ( v ) FRAGMENT TYPE: N-terminal fragment ( i x ) FEATURE:
        ( A ) NAME/KEY: Related to the sequence of the N-terminal domai
        human SLPI. In the listed sequence Xaa at position 18 is ( x i ) SEQUENCE DESCRIPTION: SEQ ID NO: 1:

```
Ser  Gly  Lys  Ser  Phe  Lys  Ala  Gly  Val  Cys  Pro  Lys  Lys  Ser  Ala  Gln
                    5                        10                            15
Cys  Xaa  Leu  Arg  Tyr  Lys  Lys  Pro  Glu  Cys  Gln  Ser  Asp  Trp  Gln  Cys
                    20                       25                       30
Pro  Gly  Lys  Lys  Arg  Cys  Cys  Pro  Asp  Thr  Cys  Gly  Ile  Lys  Cys  Leu
                    35                       40                            45
Asp
```

( 2 ) INFORMATION FOR SEQ ID NO: 2:

( i ) SEQUENCE CHARACTERISTICS:
        ( A ) LENGTH: 30 bases
        ( B ) TYPE: nucleic acid
        ( C ) STRANDEDNESS: single
        ( D ) TOPOLOGY: linear ( i i ) MOLECULE TYPE:
        - Other nucleic Acid: synthetic ( i i i ) HYPOTHETICAL: No ( i x ) FEATURE:
        ( A ) NAME/KEY: Primer for Polymerase Chain Reaction used to
        clone human SLPI.

( x i ) SEQUENCE DESCRIPTION: SEQ ID NO: 2:

GTCGCGGCCG CCTTCACCAT GAAGTCCAGC                                30

( 2 ) INFORMATION FOR SEQ ID NO: 3:

( i ) SEQUENCE CHARACTERISTICS:
        ( A ) LENGTH: 33 bases
        ( B ) TYPE: nucleic acid
        ( C ) STRANDEDNESS: single
        ( D ) TOPOLOGY: linear ( i i ) MOLECULE TYPE:
        - Other nucleic Acid: synthetic ( i i i ) HYPOTHETICAL: No ( i v ) ANTI-SENSE: No ( i x ) FEATURE:
        ( A ) NAME/KEY: Primer for Polymerase Chain Reaction used to clone human SLPI.

( x i ) SEQUENCE DESCRIPTION: SEQ ID NO: 3:

GGGGAATTCT GGCAGGAATC AAGCTTTCAC AGG                            33

( 2 ) INFORMATION FOR SEQ ID NO: 4:

( i ) SEQUENCE CHARACTERISTICS:
        ( A ) LENGTH: 30 bases
        ( B ) TYPE: nucleic acid
        ( C ) STRANDEDNESS: single
        ( D ) TOPOLOGY: linear ( i i ) MOLECULE TYPE:
        - Other nucleic Acid: synthetic ( i i i ) HYPOTHETICAL: No ( i v ) ANTI-SENSE: No ( i x ) FEATURE:
        ( A ) NAME/KEY: Primer for Polymerase Chain Reaction used to make mutein of human SLPI.

( x i ) SEQUENCE DESCRIPTION: SEQ ID NO: 4:

GGGGAATTCT CAGTTTGGGG TGTCAACAGG                                30

( 2 ) INFORMATION FOR SEQ ID NO: 5:

( i ) SEQUENCE CHARACTERISTICS:
        ( A ) LENGTH: 32 bases
        ( B ) TYPE: nucleic acid
        ( C ) STRANDEDNESS: single
        ( D ) TOPOLOGY: linear ( i i ) MOLECULE TYPE:
        - Other nucleic Acid: synthetic ( i i i ) HYPOTHETICAL: No ( i v ) ANTI-SENSE: No ( i x ) FEATURE:
        ( A ) NAME/KEY: Primer for Polymerase Chain Reaction used to make mutein of human SLPI.

( x i ) SEQUENCE DESCRIPTION: SEQ ID NO: 5:

GGGCCATGGC AACAAGGAGG AAGCCTGGGA AG                             32

( 2 ) INFORMATION FOR SEQ ID NO: 6:

( i ) SEQUENCE CHARACTERISTICS:
        ( A ) LENGTH: 33 bases (B) TYPE: nucleic acid
(C) STRANDEDNESS: single
(D) TOPOLOGY: linear (i i) MOLECULE TYPE:
- Other nucleic Acid: synthetic (i i i) HYPOTHETICAL: No (i v) ANTI-SENSE: No (i x) FEATURE:
(A) NAME/KEY: Primer for Polymerase Chain Reaction used to make mutein of human SLPI.

(x i) SEQUENCE DESCRIPTION: SEQ ID NO: 6:

CCCGGATCCG AATCAAGCTT TCACAGGGGA AAC           33

(2) INFORMATION FOR SEQ ID NO: 7:

(i) SEQUENCE CHARACTERISTICS:
(A) LENGTH: 80 bases
(B) TYPE: nucleic acid
(C) STRANDEDNESS: single
(D) TOPOLOGY: linear (i i) MOLECULE TYPE:
- Other nucleic Acid: synthetic (i i i) HYPOTHETICAL: No (i v) ANTI-SENSE: No (i x) FEATURE:
(A) NAME/KEY: Primer for Polymerase Chain Reaction used to make mutein of human SLPI.

(x i) SEQUENCE DESCRIPTION: SEQ ID NO: 7:

GGGCCATGGC AACAAGGAGG AAGCCTGGGA AGTGCCAGT GACTTATGGC           50

CAATGTAGGA TGCTTAACCC CCCCAATTTC           80

(2) INFORMATION FOR SEQ ID NO: 8:

(i) SEQUENCE CHARACTERISTICS:
(A) LENGTH: 34 bases
(B) TYPE: nucleic acid
(C) STRANDEDNESS: single
(D) TOPOLOGY: linear (i i) MOLECULE TYPE:
- Other nucleic Acid: synthetic (i i i) HYPOTHETICAL: No (i v) ANTI-SENSE: No (i x) FEATURE:
(A) NAME/KEY: Primer for Polymerase Chain Reaction used to make mutein of human SLPI.

(x i) SEQUENCE DESCRIPTION: SEQ ID NO: 8:

CCCGGATCCT CAAACGCAGG ATTTCCCACA CATG           34

(2) INFORMATION FOR SEQ ID NO: 9:

(i) SEQUENCE CHARACTERISTICS:
(A) LENGTH: 31 bases
(B) TYPE: nucleic acid
(C) STRANDEDNESS: single
(D) TOPOLOGY: linear (i i) MOLECULE TYPE:
- Other nucleic Acid: synthetic (  i i i  ) HYPOTHETICAL: No (  i v  ) ANTI-SENSE: No (  i x  ) FEATURE:
      ( A ) NAME/KEY: Primer for Polymerase Chain Reaction used to make mutein of human SLPI.

(  x i  ) SEQUENCE DESCRIPTION: SEQ ID NO: 9:

GGGCCATGGC CTTCAAAGCT GGAGTCTGTC C                                   31

( 2 ) INFORMATION FOR SEQ ID NO: 10:

( i ) SEQUENCE CHARACTERISTICS:
        ( A ) LENGTH: 38 bases
        ( B ) TYPE: nucleic acid
        ( C ) STRANDEDNESS: single
        ( D ) TOPOLOGY: linear ( i i ) MOLECULE TYPE:
          - Other nucleic Acid: synthetic (  i i i  ) HYPOTHETICAL: No (  i v  ) ANTI-SENSE: No (  i x  ) FEATURE:
      ( A ) NAME/KEY: Primer for Polymerase Chain Reaction used to make mutein of human SLPI.

(  x i  ) SEQUENCE DESCRIPTION: SEQ ID NO: 10:

GGGAGATCTC AATCCAGGCA TTTGATGCCA CAAGTGTC                               38

( 2 ) INFORMATION FOR SEQ ID NO: 11:

( i ) SEQUENCE CHARACTERISTICS:
        ( A ) LENGTH: 80 bases
        ( B ) TYPE: nucleic acid
        ( C ) STRANDEDNESS: single
        ( D ) TOPOLOGY: linear ( i i ) MOLECULE TYPE:
          - Other nucleic Acid: synthetic (  i i i  ) HYPOTHETICAL: No (  i v  ) ANTI-SENSE: No (  i x  ) FEATURE:
      ( A ) NAME/KEY: Primer for Polymerase Chain Reaction used to make mutein of human SLPI.

(  x i  ) SEQUENCE DESCRIPTION: SEQ ID NO: 11:

GGGCCATGGC AACAAGGAGG AAGCCTGGGA AGTGCCCAGT GACTTATGGC              50

CAATGTAAGA TGCTTAACCC CCCCAATTTC                                       80

( 2 ) INFORMATION FOR SEQ ID NO: 12:

( i ) SEQUENCE CHARACTERISTICS:
        ( A ) LENGTH: 89 bases
        ( B ) TYPE: nucleic acid
        ( C ) STRANDEDNESS: single
        ( D ) TOPOLOGY: linear ( i i ) MOLECULE TYPE:
          - Other nucleic Acid: synthetic (  i i i  ) HYPOTHETICAL: No (  i v  ) ANTI-SENSE: No (  i x  ) FEATURE:

( A ) NAME/KEY: Primer for Polymerase Chain Reaction used to
make mutein of human SLPI.

( x i ) SEQUENCE DESCRIPTION: SEQ ID NO: 12:

GGGCCATGGG CTCTGGAAAG TCCTTCAAAG CTGGAGTCTG TCCTAAGAAA       50

TCTGCCCAGT GCAGACTTAG ATACAAGAAA CCTGAGTGC                   89

( 2 ) INFORMATION FOR SEQ ID NO: 13:

( i ) SEQUENCE CHARACTERISTICS:
        ( A ) LENGTH: 89 bases
        ( B ) TYPE: nucleic acid
        ( C ) STRANDEDNESS: single
        ( D ) TOPOLOGY: linear ( i i ) MOLECULE TYPE:
        - Other nucleic Acid: synthetic ( i i i ) HYPOTHETICAL: No ( i v ) ANTI-SENSE: No ( i x ) FEATURE:
        ( A ) NAME/KEY: Primer for Polymerase Chain Reaction used to
make mutein of human SLPI.

( x i ) SEQUENCE DESCRIPTION: SEQ ID NO: 13:

GGGCCATGGG CTCTGGAAAG TCCTTCAAAG CTGGAGTCTG TCCTAAGAAA       50

TCTGCCCAGT GCAAGCTTAG ATACAAGAAA CCTGAGTGC                   89

( 2 ) INFORMATION FOR SEQ ID NO: 14:

( i ) SEQUENCE CHARACTERISTICS:
        ( A ) LENGTH: 37 bases
        ( B ) TYPE: nucleic acid
        ( C ) STRANDEDNESS: single
        ( D ) TOPOLOGY: linear ( i i ) MOLECULE TYPE:
        - Other nucleic Acid: synthetic ( i i i ) HYPOTHETICAL: No ( i v ) ANTI-SENSE: No ( i x ) FEATURE:
        ( A ) NAME/KEY: Primer for Polymerase Chain Reaction used to
make mutein of human SLPI.

( x i ) SEQUENCE DESCRIPTION: SEQ ID NO: 14:

GGGGGGGAAT TCTCAAACGC AGGATTTCCC ACACATG                     37

( 2 ) INFORMATION FOR SEQ ID NO: 15:

( i ) SEQUENCE CHARACTERISTICS:
        ( A ) LENGTH: 93 bases
        ( B ) TYPE: nucleic acid
        ( C ) STRANDEDNESS: single
        ( D ) TOPOLOGY: linear ( i i ) MOLECULE TYPE:
        - Other nucleic Acid: synthetic ( i i i ) HYPOTHETICAL: No ( i v ) ANTI-SENSE: No ( i x ) FEATURE:
        ( A ) NAME/KEY: Primer for Polymerase Chain Reaction used to
make mutein of human SLPI.

( x i ) SEQUENCE DESCRIPTION: SEQ ID NO: 15:

```
GGGGGGCCAT  GGGCTCTGGA  AAGTCCTTCA  AAGCTGGAGT  CTGTCCTCCT                50

AAGAAATCTG  CCCAGTGCAG  AAGATACAAG  AAACCTGAGT  GCC                       93
```

( 2 ) INFORMATION FOR SEQ ID NO: 16:

( i ) SEQUENCE CHARACTERISTICS:
     ( A ) LENGTH: 93 bases
     ( B ) TYPE: nucleic acid
     ( C ) STRANDEDNESS: single
     ( D ) TOPOLOGY: linear ( i i ) MOLECULE TYPE:
     - Other nucleic Acid: synthetic ( i i i ) HYPOTHETICAL: No ( i v ) ANTI-SENSE: No ( i x ) FEATURE:
     ( A ) NAME/KEY: Primer for Polymerase Chain Reaction used to
         make mutein of human SLPI.

( x i ) SEQUENCE DESCRIPTION: SEQ ID NO: 16:

```
GGGGGGCCAT  GGGCTCTGGA  AAGTCCTTCA  AAGCTGGAGT  CTGTCCTCCT                50

AAGAAATCTG  CCCAGTGCAA  GAGATACAAG  AAACCTGAGT  GCC                       93
```

( 2 ) INFORMATION FOR SEQ ID NO: 17:

( i ) SEQUENCE CHARACTERISTICS:
     ( A ) LENGTH: 10 amino acids
     ( B ) TYPE: amino acid
     ( D ) TOPOLOGY: linear ( i i ) MOLECULE TYPE:
     ( A ) DESCRIPTION:
       - protein.

( i i i ) HYPOTHETICAL: No ( v ) FRAGMENT TYPE: internal fragment ( v i ) ORIGINAL SOURCE:
     ( A ) ORGANISM: human
     ( F ) TISSUE TYPE: nasal secretions ( i x ) FEATURE:
     ( A ) NAME/KEY: N-terminal sequence analysis of the naturally
         occurring inhibitor of mast cell tryptase that
         was purified from human nasal secretions.
         Sequence corresponds to an internal fragment of
         human SLPI beginning at residue number 73.
     ( C ) IDENTIFICATION METHOD: by experiment as well as by
         similarity to known sequence.

( x i ) SEQUENCE DESCRIPTION: SEQ ID NO: 17:

```
          Xaa  Leu  Asn  Pro  Pro  Asn  Phe  Xaa  Xaa  Xaa
            5                      10
```

( 2 ) INFORMATION FOR SEQ ID NO: 18:

( i ) SEQUENCE CHARACTERISTICS:
     ( A ) LENGTH: 10 amino acids
     ( B ) TYPE: amino acid
     ( D ) TOPOLOGY: linear ( i i ) MOLECULE TYPE:
     ( A ) DESCRIPTION:
       - protein ( i i i ) HYPOTHETICAL: No ( v ) FRAGMENT TYPE: N-terminal fragment (v i) ORIGINAL SOURCE:
    (A) ORGANISM: Human
    (F) TISSUE TYPE: Nasal secretions (i x) FEATURE:
    (A) NAME/KEY: N-terminal sequence analysis of the naturally
        occurring inhibitor of mast cell tryptase that
        was purified from human nasal secretions.
        Sequence corresponds to the N-terminal sequence
        of human SLPI.
    (C) IDENTIFICATION METHOD: by experiment, as well as by
        similarity to known sequence.

(x i) SEQUENCE DESCRIPTION: SEQ ID NO: 18:

Xaa  Gly  Lys  Xaa  Phe  Lys  Ala  Gly  Val  Xaa
          5                        10

(2) INFORMATION FOR SEQ ID NO: 19:

(i) SEQUENCE CHARACTERISTICS:
        (A) LENGTH: 10 amino acids
        (B) TYPE: amino acid
        (D) TOPOLOGY: linear (i i) MOLECULE TYPE:
        (A) DESCRIPTION:
            - protein (i i i) HYPOTHETICAL: No (v) FRAGMENT TYPE: N-terminal fragment (v i) ORIGINAL SOURCE:
        (A) ORGANISM: Human (i x) FEATURE:
        (A) NAME/KEY: N-terminal sequence analysis of the naturally
            occurring inhibitor of mast cell tryptase that
            was purified from human nasal secretions.
        (C) IDENTIFICATION METHOD: by experiment, as well as by
            similarity to known sequence.

(x i) SEQUENCE DESCRIPTION: SEQ ID NO: 19:

Xaa  Gly  Lys  Xaa  Phe  Lys  Ala  Gly  Xaa  Xaa
          5                        10

(2) INFORMATION FOR SEQ ID NO: 20:

(i) SEQUENCE CHARACTERISTICS:
        (A) LENGTH: 11 amino acids
        (B) TYPE: amino acid
        (D) TOPOLOGY: linear (i i) MOLECULE TYPE:
        (A) DESCRIPTION:
            - peptide.

(i i i) HYPOTHETICAL: No (i x) FEATURE:
        (A) NAME/KEY: Synthetic peptide substrate used in the assay
            to measure the proteolytic activity of mast
            cell tryptase.
        (D) OTHER INFORMATION: actual peptide contains 2-aminobenzoyl
            (anthranilyl) (Abz) at the N-terminus and the
            modified amino acids p-nitrophenylalanine at
            position 7 and norleucine at position 10.
            There is an NH2 group at the C-terminus.

(x i) SEQUENCE DESCRIPTION: SEQ ID NO: 20:

His  Lys  Ala  Arg  Val  Leu  Xaa  Glu  Ala  Xaa  Ser
          5                        10

(2) INFORMATION FOR SEQ ID NO: 21:

(i) SEQUENCE CHARACTERISTICS:
    (A) LENGTH: 132
    (B) TYPE: amino acid
    (D) TOPOLOGY: linear (ii) MOLECULE TYPE:
    (A) DESCRIPTION:
      - protein (iii) HYPOTHETICAL: No (vi) ORIGINAL SOURCE:
    (A) ORGANISM: Human (ix) FEATURE:
    (A) NAME/KEY: Complete amino acid sequence of human SLPI
        (antileukoprotease).

(x) PUBLICATION INFORMATION:
    (A) AUTHORS: Heinzel, R., Appelhans, H., Gassen, G.,
                 Seemuller, U., Machleidt, W., Fritz, H., and
                 Steffens, G.
    (B) TITLE: Molecular cloning and expression of cDNA for human
               antileukoprotease from cervix uterus
    (C) JOURNAL: European Journal of Biochemistry
    (D) VOLUME: 160
    (F) PAGES: 61-67
    (G) DATE: 1986

(xi) SEQUENCE DESCRIPTION: SEQ ID NO: 21:

```
Met  Lys  Ser  Ser  Gly  Leu  Phe  Pro  Phe  Leu  Val  Leu  Leu  Ala  Leu  Gly
-25                 -20                      -15                           -10

Thr  Leu  Ala  Pro  Trp  Ala  Val  Glu  Gly  Ser  Gly  Lys  Ser  Phe  Lys  Ala
 -5                  1                   5

Gly  Val  Cys  Pro  Pro  Lys  Lys  Ser  Ala  Gln  Cys  Leu  Arg  Tyr  Lys  Lys
 10                 15                       20

Pro  Glu  Cys  Gln  Ser  Asp  Trp  Gln  Cys  Pro  Gly  Lys  Lys  Arg  Cys  Cys
 25                  30                       35

Pro  Asp  Thr  Cys  Gly  Ile  Lys  Cys  Leu  Asp  Pro  Val  Asp  Thr  Pro  Asn
 40                 45                       50                            55

Pro  Thr  Arg  Arg  Lys  Pro  Gly  Lys  Cys  Pro  Val  Thr  Tyr  Gly  Gln  Cys
 60                 65                       70

Leu  Met  Leu  Asn  Pro  Pro  Asn  Phe  Cys  Glu  Met  Asp  Gly  Gln  Cys  Lys
 75                 80                       85

Arg  Asp  Leu  Lys  Cys  Cys  Met  Gly  Met  Cys  Gly  Lys  Ser  Cys  Val  Ser
 90                 95                       100

Pro  Val  Lys  Ala
105
```